United States Patent
Fogarty et al.

(10) Patent No.: US 9,561,037 B2
(45) Date of Patent: Feb. 7, 2017

(54) EMBOLIZATION DEVICE AND A METHOD OF USING THE SAME

(75) Inventors: Thomas J. Fogarty, Portola Valley, CA (US); Michael J. Drews, Palo Alto, CA (US); D. Bruce Modesitt, San Carlos, CA (US); Neil Bruce Holmgren, Chicago, IL (US); David B. Willis, Palo Alto, CA (US)

(73) Assignee: Thomas J. Fogarty, Mountain View, CA (US)

( * ) Notice: Subject to any disclaimer, the term of this patent is extended or adjusted under 35 U.S.C. 154(b) by 0 days.

(21) Appl. No.: 13/180,420

(22) Filed: Jul. 11, 2011

(65) Prior Publication Data

US 2012/0179192 A1    Jul. 12, 2012

Related U.S. Application Data

(63) Continuation of application No. 10/622,437, filed on Jul. 18, 2003, now abandoned.

(51) Int. Cl.
| | | |
|---|---|---|
| *A61M 29/00* | (2006.01) | |
| *A61B 17/12* | (2006.01) | |
| *A61F 2/07* | (2013.01) | |
| *A61L 31/04* | (2006.01) | |
| *A61F 2/88* | (2006.01) | |

(52) U.S. Cl.
CPC ... *A61B 17/12118* (2013.01); *A61B 17/12022* (2013.01); *A61B 17/12163* (2013.01); *A61F 2/07* (2013.01); *A61F 2/88* (2013.01); *A61L 31/044* (2013.01); *A61F 2002/075* (2013.01); *A61F 2220/0091* (2013.01); *A61F 2230/001* (2013.01)

(58) Field of Classification Search
CPC ............... A61B 17/12022; A61B 17/12163; A61B 17/12109; A61B 17/12113; A61B 17/12118; A61F 2220/0091; A61F 2230/0019; A61F 2230/0021; Y10R 403/32032; A44C 11/002; A44C 5/08
USPC ........................................ 606/108, 194, 200
See application file for complete search history.

(56) References Cited

U.S. PATENT DOCUMENTS

| | | |
|---|---|---|
| 2,903,365 A | 9/1959 | O'Brian et al. |
| 4,301,803 A | 11/1981 | Handa et al. |
| 4,346,712 A | 8/1982 | Handa et al. |
| 4,638,803 A | 1/1987 | Rand |

(Continued)

FOREIGN PATENT DOCUMENTS

| | | |
|---|---|---|
| AU | 2003/204493 | 12/2003 |
| WO | WO 01/06950 | 2/2001 |

(Continued)

OTHER PUBLICATIONS

Franklin et al, "Uptake of Tetracycline by Aortic Aneurysm Wall and Its Effect on Inflammation and Proteolysis," *Brit. J. Surgery*, 86(6):771-775, 1999.

(Continued)

*Primary Examiner* — Katherine Rodjom
(74) *Attorney, Agent, or Firm* — Levine Bagade Han LLP

(57) ABSTRACT

Space-occupying devices for treating voids within the body are disclosed. The devices can have multiple elements connected to a flexible leader. The devices can be coated by a binding agent. The devices can also be fillable. Methods of making and using the devices are also disclosed.

17 Claims, 13 Drawing Sheets

(56) References Cited

U.S. PATENT DOCUMENTS

| | | | |
|---|---|---|---|
| 4,641,653 A | 2/1987 | Rockey | |
| 4,728,328 A | 3/1988 | Hughes et al. | |
| 4,944,745 A | 7/1990 | Sogard et al. | |
| 4,994,069 A * | 2/1991 | Ritchart et al. | 606/191 |
| 5,133,731 A | 7/1992 | Butler et al. | |
| 5,151,105 A | 9/1992 | Kwan-Gett | |
| 5,156,620 A | 10/1992 | Pigott | |
| 5,226,911 A | 7/1993 | Chee et al. | |
| 5,282,824 A | 2/1994 | Gianturco | |
| 5,308,356 A | 5/1994 | Blackshear, Jr. et al. | |
| 5,312,415 A | 5/1994 | Palermo | |
| 5,330,528 A | 7/1994 | Lazim | |
| 5,395,333 A | 3/1995 | Brill | |
| 5,411,550 A | 5/1995 | Herweck et al. | |
| 5,478,309 A | 12/1995 | Sweezer et al. | |
| 5,530,528 A | 6/1996 | Houki et al. | |
| 5,534,024 A | 7/1996 | Rogers et al. | |
| 5,540,711 A * | 7/1996 | Kieturakis | A61B 17/0218 600/204 |
| 5,558,642 A | 9/1996 | Schweich, Jr. et al. | |
| 5,582,619 A | 12/1996 | Ken | |
| 5,613,981 A | 3/1997 | Boyle et al. | |
| 5,665,117 A | 9/1997 | Rhodes | |
| 5,667,767 A | 9/1997 | Greff et al. | |
| 5,693,088 A | 12/1997 | Lazarus | |
| 5,702,361 A | 12/1997 | Evans et al. | |
| 5,713,917 A | 2/1998 | Leonhardt et al. | |
| 5,725,568 A | 3/1998 | Hastings | |
| 5,749,894 A | 5/1998 | Engelson | |
| 5,752,974 A | 5/1998 | Rhee et al. | |
| 5,766,160 A | 6/1998 | Samson et al. | |
| 5,769,882 A | 6/1998 | Fogarty et al. | |
| 5,785,679 A | 7/1998 | Abolfathi et al. | |
| 5,795,331 A | 8/1998 | Cragg et al. | |
| 5,823,198 A | 10/1998 | Jones et al. | |
| 5,824,037 A | 10/1998 | Fogarty et al. | |
| 5,830,230 A * | 11/1998 | Berryman et al. | 606/200 |
| 5,843,160 A | 12/1998 | Rhodes | |
| 5,876,448 A | 3/1999 | Thompson et al. | |
| 5,916,235 A | 6/1999 | Guglielmi | |
| 5,925,059 A | 7/1999 | Palermo et al. | |
| 5,928,260 A | 7/1999 | Chin et al. | |
| 5,935,145 A | 8/1999 | Villar et al. | |
| 5,944,733 A | 8/1999 | Engelson | |
| 5,951,599 A | 9/1999 | McCrory | |
| 5,980,514 A | 11/1999 | Kupiecki et al. | |
| 5,984,963 A | 11/1999 | Ryan et al. | |
| 5,994,750 A | 11/1999 | Yagi | |
| 6,015,424 A | 1/2000 | Rosenbluth et al. | |
| 6,024,754 A | 2/2000 | Engelson | |
| 6,066,149 A | 5/2000 | Samson et al. | |
| 6,093,199 A | 7/2000 | Brown et al. | |
| 6,096,021 A | 8/2000 | Helm et al. | |
| 6,110,198 A | 8/2000 | Fogarty et al. | |
| 6,113,629 A | 9/2000 | Ken | |
| 6,139,520 A | 10/2000 | McCrory et al. | |
| 6,146,373 A | 11/2000 | Cragg et al. | |
| 6,149,664 A | 11/2000 | Kurz | |
| 6,165,193 A | 12/2000 | Greene, Jr. et al. | |
| 6,165,194 A | 12/2000 | Denardo | |
| 6,168,592 B1 | 1/2001 | Kupiecki et al. | |
| 6,190,402 B1 | 2/2001 | Horton et al. | |
| 6,193,745 B1 | 2/2001 | Fogarty et al. | |
| 6,196,230 B1 | 3/2001 | Hall et al. | |
| 6,203,550 B1 | 3/2001 | Olson | |
| 6,203,779 B1 | 3/2001 | Ricci et al. | |
| 6,231,562 B1 | 5/2001 | Khosravi et al. | |
| 6,238,403 B1 | 5/2001 | Greene, Jr. et al. | |
| 6,261,305 B1 | 7/2001 | Marotta et al. | |
| 6,273,917 B1 | 8/2001 | Inoue | |
| 6,283,991 B1 | 9/2001 | Cox et al. | |
| 6,287,315 B1 | 9/2001 | Wijeratne et al. | |
| 6,293,960 B1 | 9/2001 | Ken | |
| 6,296,603 B1 | 10/2001 | Turnlund et al. | |
| 6,296,604 B1 | 10/2001 | Garibaldi et al. | |
| 6,299,597 B1 | 10/2001 | Buscemi et al. | |
| 6,299,619 B1 | 10/2001 | Greene, Jr. et al. | |
| 6,312,421 B1 | 11/2001 | Boock | |
| 6,312,462 B1 | 11/2001 | McDermott et al. | |
| 6,312,463 B1 | 11/2001 | Rourke et al. | |
| 6,315,709 B1 | 11/2001 | Garibaldi et al. | |
| 6,331,184 B1 | 12/2001 | Abrams | |
| 6,334,869 B1 | 1/2002 | Leonhardt et al. | |
| 6,344,041 B1 | 2/2002 | Kupiecki et al. | |
| 6,344,048 B1 | 2/2002 | Chin et al. | |
| 6,350,270 B1 * | 2/2002 | Roue | A61B 17/12022 606/151 |
| 6,358,556 B1 | 3/2002 | Ding et al. | |
| 6,364,823 B1 | 4/2002 | Garibaldi et al. | |
| 6,375,668 B1 * | 4/2002 | Gifford | A61B 17/12022 606/200 |
| 6,375,669 B1 * | 4/2002 | Rosenbluth et al. | 606/200 |
| 6,379,329 B1 | 4/2002 | Naglreiter et al. | |
| 6,383,174 B1 | 5/2002 | Eder | |
| 6,395,019 B2 | 5/2002 | Chobotov | |
| 6,458,119 B1 | 10/2002 | Berenstein et al. | |
| 6,463,317 B1 | 10/2002 | Kucharczyk et al. | |
| 6,506,204 B2 | 1/2003 | Mazzocchi | |
| 6,511,468 B1 | 1/2003 | Cragg et al. | |
| 6,521,244 B1 | 2/2003 | Kanesaka | |
| 6,527,739 B1 | 3/2003 | Bigus et al. | |
| 6,544,276 B1 | 4/2003 | Azizi | |
| 6,551,280 B1 | 4/2003 | Knighton et al. | |
| 6,558,367 B1 | 5/2003 | Cragg et al. | |
| 6,589,265 B1 | 7/2003 | Palmer et al. | |
| 6,592,614 B2 | 7/2003 | Lenker et al. | |
| 6,613,037 B2 | 9/2003 | Khosravi et al. | |
| 6,613,074 B1 | 9/2003 | Mitelberg et al. | |
| 6,616,684 B1 | 9/2003 | Vidlund et al. | |
| 6,626,928 B1 | 9/2003 | Raymond et al. | |
| 6,629,947 B1 | 10/2003 | Sahatjian et al. | |
| 6,645,167 B1 | 11/2003 | Whalen, II et al. | |
| 6,656,214 B1 | 12/2003 | Fogarty et al. | |
| 6,663,607 B2 | 12/2003 | Slaikeu et al. | |
| 6,663,667 B2 | 12/2003 | Dehdashtian et al. | |
| 6,692,510 B2 | 2/2004 | West | |
| 6,695,876 B1 | 2/2004 | Marotta et al. | |
| 6,712,826 B2 | 3/2004 | Lui | |
| 6,723,108 B1 | 4/2004 | Jones et al. | |
| 6,730,119 B1 * | 5/2004 | Smalling | A61F 2/07 606/194 |
| 6,827,735 B2 | 12/2004 | Greenberg | |
| 6,843,803 B2 | 1/2005 | Ryan et al. | |
| 6,852,097 B1 | 2/2005 | Fulton, III | |
| 6,921,410 B2 | 7/2005 | Porter | |
| 7,070,609 B2 | 7/2006 | West | |
| 7,081,129 B2 | 7/2006 | Chobotov | |
| 7,128,736 B1 | 10/2006 | Abrams et al. | |
| 7,147,660 B2 | 12/2006 | Chobotov et al. | |
| 7,147,661 B2 | 12/2006 | Chobotov et al. | |
| 7,530,988 B2 | 5/2009 | Evans et al. | |
| 7,615,071 B2 | 11/2009 | Chobotov | |
| 8,231,665 B2 | 7/2012 | Kim et al. | |
| 8,231,666 B2 | 7/2012 | Kim et al. | |
| 8,262,686 B2 | 9/2012 | Fogarty et al. | |
| 8,361,136 B2 | 1/2013 | Chobotov | |
| 8,647,377 B2 | 2/2014 | Kim et al. | |
| 8,801,769 B2 | 8/2014 | Chobotov | |
| 2001/0020184 A1 | 9/2001 | Dehdashtian et al. | |
| 2001/0047202 A1 | 11/2001 | Slaikeu et al. | |
| 2002/0019665 A1 | 2/2002 | Dehdashtian et al. | |
| 2002/0026217 A1 | 2/2002 | Baker et al. | |
| 2002/0045848 A1 | 4/2002 | Jaafar et al. | |
| 2002/0052643 A1 | 5/2002 | Wholey et al. | |
| 2002/0065542 A1 | 5/2002 | Lax et al. | |
| 2002/0082638 A1 * | 6/2002 | Porter | A61B 17/12113 606/195 |
| 2002/0169497 A1 | 11/2002 | Wholey et al. | |
| 2002/0193821 A1 * | 12/2002 | Trout, III | A61B 17/11 606/194 |
| 2003/0004531 A1 * | 1/2003 | Jones | A61B 17/12022 606/191 |
| 2003/0014075 A1 | 1/2003 | Rosenbluth et al. | |

(56) References Cited

U.S. PATENT DOCUMENTS

| | | |
|---|---|---|
| 2003/0028209 A1* | 2/2003 | Teoh ................ A61B 17/12022 606/191 |
| 2003/0051735 A1 | 3/2003 | Pavcnik et al. |
| 2003/0074017 A1* | 4/2003 | Shah ................ A61M 25/1029 606/194 |
| 2003/0204246 A1 | 10/2003 | Chu et al. |
| 2003/0216802 A1 | 11/2003 | Chobotov |
| 2003/0220666 A1* | 11/2003 | Mirigian .......... A61B 17/12022 606/200 |
| 2003/0229286 A1* | 12/2003 | Lenker .......................... 600/462 |
| 2004/0044358 A1 | 3/2004 | Khosravi et al. |
| 2004/0044361 A1* | 3/2004 | Frazier ................ A61B 17/0057 606/200 |
| 2004/0098027 A1 | 5/2004 | Teoh et al. |
| 2004/0116997 A1 | 6/2004 | Taylor et al. |
| 2004/0210249 A1 | 10/2004 | Fogarty et al. |
| 2004/0254625 A1* | 12/2004 | Stephens .......... A61B 17/12022 623/1.1 |
| 2006/0292206 A1* | 12/2006 | Kim ................ A61B 17/12022 424/443 |
| 2007/0050008 A1 | 3/2007 | Kim et al. |
| 2007/0055355 A1 | 3/2007 | Kim et al. |
| 2007/0061005 A1 | 3/2007 | Kim et al. |
| 2008/0275536 A1 | 11/2008 | Zarins et al. |
| 2012/0265287 A1 | 10/2012 | Sharma et al. |
| 2014/0081374 A1 | 3/2014 | Kim et al. |
| 2014/0142685 A1 | 5/2014 | Kim et al. |

FOREIGN PATENT DOCUMENTS

| | | |
|---|---|---|
| WO | WO 01/28434 | 4/2001 |
| WO | WO 0193920 A2 * | 12/2001 |
| WO | WO 02/102282 | 12/2002 |
| WO | WO 2004/045393 | 6/2004 |

OTHER PUBLICATIONS

Pyo et al, "Targeted Gene Disruption of Matrix Metalloproteinase-9 (Gelatinase B) Suppresses Development of Experimental Abdominal Aortic Aneurysms," *J. Clinical Investigation*, 105(11):1641-1649, 2000.

Tambiah et al, "Provocation of Experimental Aortic Inflammation Mediators and Chlamydia Pneumoniae," *Brit. J. Surgery*, 88(7):935-940, 2001.

Villareal et al, "Early Results Using Bare Metal Stents With or Without Coil Embolization for AAA Exclusion," *Journal of endovascular therapy : an official journal of the International Society of Endovascular Specialists*,8 pages, 2001.

Walton, et al, "Inhibition of Prostoglandin E2 Synthesis in Abdominal Aortic Aneurysms," *Circulation*, pp. 48-54, Jul. 6, 1999.

Xu et al, "Sp 1 Increases Expression of Cyclooxygenase-2 in Hypoxic Vascular Endothelium," *J. Biological Chemistry*, 275(32):24583-24589, 2000.

\* cited by examiner

NOT INVENTION

NOT INVENTION

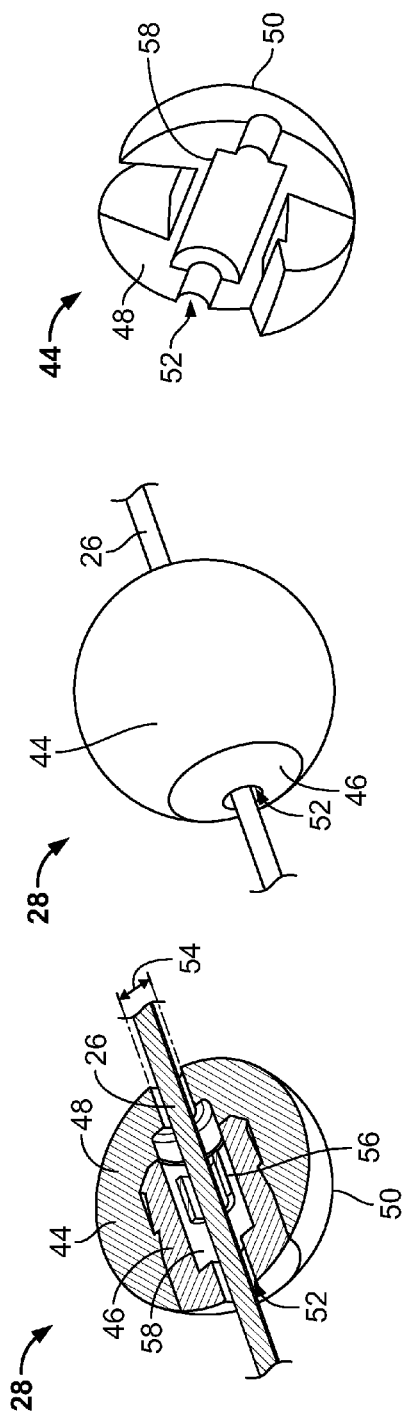
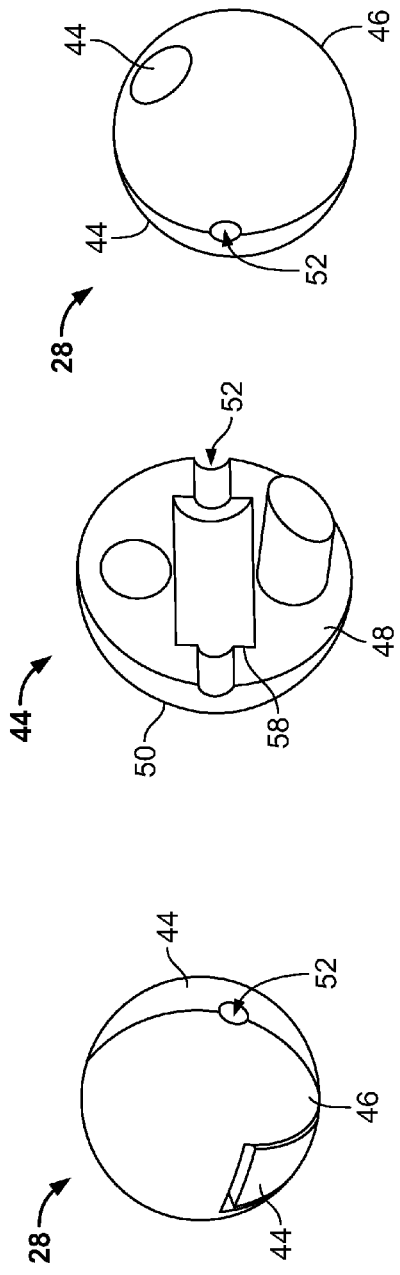

EMBOLIZATION DEVICE AND A METHOD OF USING THE SAME

CROSS-REFERENCE TO RELATED APPLICATIONS

This application is a continuation of U.S. patent application Ser. No. 10/622,437, filed on Jul. 18, 2003, now abandoned, the content of which is incorporated herein by reference in its entirety.

BACKGROUND OF THE INVENTION

Field of the Invention

The present invention relates generally to a device for filling and/or stabilizing the void within an anatomical organ of the body, particularly within the vasculature, and methods for making and using the device.

Description of the Related Art

An aneurysm is an abnormal dilatation of a biological vessel. Aneurysms can alter flow through the affected vessel and often decrease the strength of the vessel wall, thereby increasing the vessel's risk of rupturing at the point of dilation or weakening. FIG. 1 illustrates an abdominal aorta 2 with a sacular aneurysm 4 having an aneurysm wall 6. FIG. 2 illustrates the abdominal aorta 2 with a vascular prosthesis 8 implanted to treat the aneurysm 4, a common aneurysm therapy. Vascular grafts and stent-grafts (e.g., ANEURX® Stent Graft System from Medtronic AVE, Inc., Santa Rosa, Calif.) are examples of vascular prostheses used to treat aneurysms by reconstructing the damaged vessel.

With the prosthesis 8 implanted, an aneurysm sac 10 is defined by the volume between the prosthesis 8 and the aneurysm wall 6. The sac 10 is often filled, partially or completely, with thrombi 12. The thrombi 12 can be partially removed prior to deploying the prosthesis 8. Whether the thrombi 12 are removed, gaps exist between the remaining thrombi 12 or the aneurysm wall 6 and the prosthesis 8, and even when thrombus is present, it can be soft and non-structural. The prosthesis 8 can dislodge or migrate due to the poor fit caused by these gaps and shrinkage of the sac 10 that occurs after the implantation of the prosthesis 8, either acutely due to sizing issues, or over time due to reformation of the sac 10. To reduce the risk of prosthesis dislodgement and migration, the sac 10 can be filled to stabilize the anatomy adjacent to the prosthesis 8 resulting in better efficacy of the prosthetic treatment.

A sac filler, or stabilizer, can be introduced to the sac 10 by trans-graft, trans-collateral, trans-sac, or endoluminal procedures. The trans-graft procedure introduces the sac filler through an opening in the prosthesis 8, as shown by arrows 12. The trans-collateral procedure, shown by arrows 16, introduces the sac filler through a collateral vessel 18 under fluoroscopic guidance that is in direct communication with the sac 10. The trans-sac procedure, often performed laparoscopically, introduces the sac filler through a puncture in the wall 6 of the aneurysm, as shown by arrows 20. The endoluminal procedure introduces the sac filler through the vessel that has the aneurysm 4, as shown by arrows 22, but within the space between the prosthesis and the vessel wall. The trans-graft, trans-collateral and endoluminal procedures are often performed as minimally invasive, entirely endovascular procedures.

It is desirable for a stabilizing element or sac filler to conform to the available space within the sac 10 by operation of the geometry of the device (e.g., by nesting or coiling) and/or by any coatings or materials utilized to promote fusing or other coagulative effect.

U.S. Pat. No. 6,146,373 to Cragg et al. discloses a catheter system and method for injecting a liquid embolic composition and a solidification agent directly into a sac. Cragg et al. teach the use of organic solvents such as DMSO, ethanol and others injected directly in the aneurysm. Cragg et al. teach that these solvents can be toxic to tissue and may cause vascular spasms. Using liquid-solidifying agents in active vessels also carries a high risk that the agents will flow downstream creating emboli or flow into collateral vessels (e.g., lumbar arteries), which may lead to paralysis or other adverse events.

U.S. Pat. No. 4,994,069 to Ritchart et al., U.S. Pat. No. 5,133,731 to Butler et al., U.S. Pat. No. 5,226,911 to Chee et al., and U.S. Pat. No. 5,312,415 to Palermo disclose examples of thrombogenic microcoils, common aneurysm treatments. The microcoil must be tightly packed into the aneurysm to minimize shifting of the microcoils. Shifting of the microcoil can lead to recanalization of the aneurysm. Another disadvantage of microcoils is that they are not easily retrievable. If a coil migrates out of the aneurysm, a second procedure to retrieve the coil and move the coil back into place, or replace the coil, might be necessary.

U.S. Pat. Nos. 6,238,403 and 6,299,619, both to Greene, Jr. et al., disclose an embolic device with expansible elements and methods for embolizing a target vascular site with the device. The device taught by Greene Jr. includes a plurality of highly-expansible elements disposed at spaced intervals along a filamentous carrier. The expansion of the device after deployment reduces the volumetric precision with which the sac can be filled. If the volume of the expanded device is too large, the device can press against the inner side of weakened aneurysm wall and outer side of prosthesis, altering flow within the prosthesis and increasing the risk of rupture of the aneurysm. If the volume of the expanded device is too small, the prosthesis can still alter its position and dislodge or migrate.

There is thus a need for a device and method that can precisely occlude a known sac volume with minimal displacement of the device over time. There is also a need for a device that can be deployed to the sac 10 while simultaneously minimizing toxicity, embolism risk, and other disadvantages previously associated with existing aneurysm sac fillers.

BRIEF SUMMARY OF THE INVENTION

A vascular embolization device having a flexible leader connected to at least one non-expandable, space-occupying element is disclosed. The elements can be made, for example, from collagen and/or a polymer such as polypropylene. The device can also have a radiopaque agent fixed to or integrated with the device. Furthermore, the device can be coated or infused with a therapeutic and/or diagnostic agent.

A vascular embolization device having a leader made from a flexible material and a space-occupying element connected to the leader is also disclosed. The element has a first component secured to a second component. The element can also be slidably connected to the leader, for example, by a ferrule.

A vascular embolization device having one or more cylindrical space-occupying elements connected by flexible helical segments is disclosed. When fully extended, the element has a cross-sectional width to cross-sectional height ratio of equal to or greater than about 1.5:1. The cross-sectional width-to-height ratio can also be equal to or greater than 4:1.

A vascular embolization device having a first space-occupying element having a first male interference-fit piece, and a second space-occupying element having a first female interference-fit piece is disclosed as well. The first male interference-fit piece and the first female interference-fit piece attach to impede removal of the first male interference-fit piece from the first female interference-fit piece.

A vascular embolization device is also disclosed. The device has a first space-occupying element comprising a body and a first female interference-fit piece. The device also has a second space-occupying element comprising a body and a second female interference-fit piece. Furthermore, the device has a leader comprising a first male interference-fit piece on a first end and a second male interference-fit piece on a second end. The first male interference-fit piece attaches to the first female interference-fit piece and the second male interference-fit piece attaches to the second female interference-fit piece.

A device volume for filling an abnormal void within the body including a bindging agent is disclosed. The device volume is all or part of the volume of the device. The device has a first space-occupying piece, a second space-occupying piece and a binding agent. The first space-occupying piece is flexibly attached to the second space-occupying piece such as a continuous structure, such as a coil. The binding agent attaches the first space-occupying piece and the second space-occupying piece (e.g., each turn of the coil). The binding agent reduces the flexibility of the device volume and increases the pushability to aid in deployment. The flexibility of the device volume of the first space-occupying piece and the second space-occupying piece is restored when the binding agent is exposed to a softening agent.

First and second pieces of the device can also have a flexible leader. The leader can connect to the first space-occupying piece at a first length along the leader. The leader can also connect to the second space-occupying piece at a second length along the leader. The leader can have a first end integrated with the first space-occupying piece and a second end integrated with the second space-occupying piece. The leader can have a first end attached to the first space-occupying piece to impede removal of the first space-occupying piece from the leader, for example, the leader can have a knot. The first and second space-occupying pieces can also either or both be non-expandable or expandable based on the desired clinical result.

A space-occupying device having a flexible segment is disclosed. The segment is maintained in a substantially cylindrical configuration by a binding agent. The flexibility of the helical segment is increased when the binding agent is exposed to a softening agent. The flexible segment can have a helical segment. The flexible segment can also have a woven segment.

A device for filling an abnormal void within the body is also disclosed. The device has a fillable bladder and a filling agent. The fillable bladder can be pressurized or otherwise occupied with the filling agent. The bladder can be porous.

A method is disclosed for placing a space-occupying device or a plurality of space-occupying devices, such as the embolization devices disclosed herein, within a void. For example, a catheter having a distal exit is placed at a vascular site. A vascular embolization device is then passed through the catheter and the distal exit and deployed into the vascular site. The device has a flexible leader and at least one non-expandable, space-occupying elements connected to the leader. The method can include selecting a device or devices having the proper volume so that the device(s) is large enough to substantially fill the void, such as an aneurysmal sac within the vasculature, yet small enough to prevent substantial alteration of the natural fluid flow through an adjacent element, for example a vascular prosthesis implanted at or near the vascular site. Furthermore, the method of the present invention may provide for the removal of material within the void, such as the removal of thrombus from the aneurysmal sac and treatment with therapeutic agents prior to, or in conjunction with, the placement of the space-occupying elements.

A method is also disclosed for filling an abnormal void within the body. The method includes placing a catheter having a distal exit in a void within the body. The method also includes passing a space-occupying device through the catheter and distal exit. The space-occupying device comprising a device volume and a binding agent. The binding agent reduces the flexibility of the space-occupying device. The distal exit of the device is placed at a treatment site at the time of deployment to aid in ejection of the space-occupying device from the delivery catheter.

The flexibility of the space-occupying device can also increase when the binding agent is exposed to a softening agent. Deploying the device can include exposing the device to a softening agent.

Another method is disclosed for filling an abnormal void within the body. The method includes deploying a device into the void. The device has a fillable volume. The method also includes filling the fillable volume with a filling agent. Filling the fillable volume can include using a filling agent such as a gel. Filling can include filling with a filling agent in the form of pieces or particulate. The pieces or particulate can be contained by the fillable volume. The pieces or particulate can have a smaller diameter than branch vessels and the pieces or particulate can be expandable. Filling can include filling with a filling agent in a flowable form. The method can also include hardening the filling agent.

BRIEF DESCRIPTION OF THE DRAWINGS

FIG. 3b illustrates a portion of the embolization device of FIG. 3a.

FIG. 4 is a cross-sectional view of an embodiment of the leader and the space-occupying element.

FIG. 5 illustrates an embodiment of the leader and the space-occupying element of FIG. 4.

FIG. 6 illustrates an embodiment of the first section of the space-occupying element.

FIG. 7 illustrates an embodiment of the space-occupying element of FIG. 6.

FIG. 8 illustrates an embodiment of the first section of the space-occupying element.

FIG. 9 illustrates an embodiment of the space-occupying element of FIG. 8.

DETAILED DESCRIPTION

Figure 1:
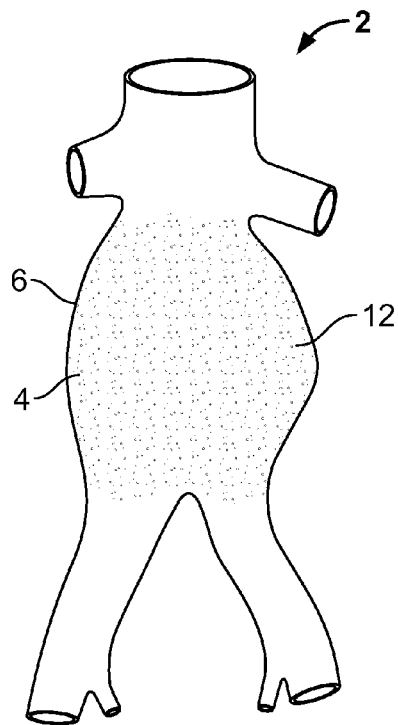
FIG. 1, not the invention, illustrates an aneurysm.
Figure 2:
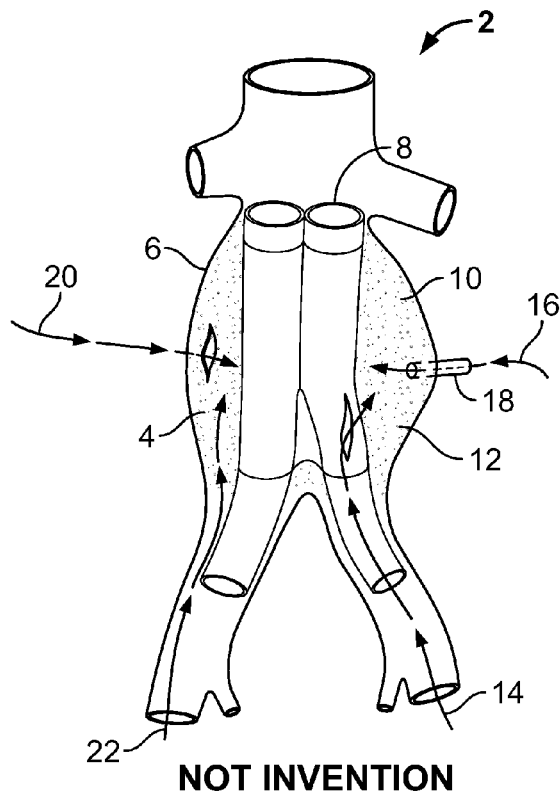
FIG. 2, not the invention, illustrates a vascular prosthesis implanted within an aneurysm and procedures for filling the aneurysm sac.
Figure 3A:
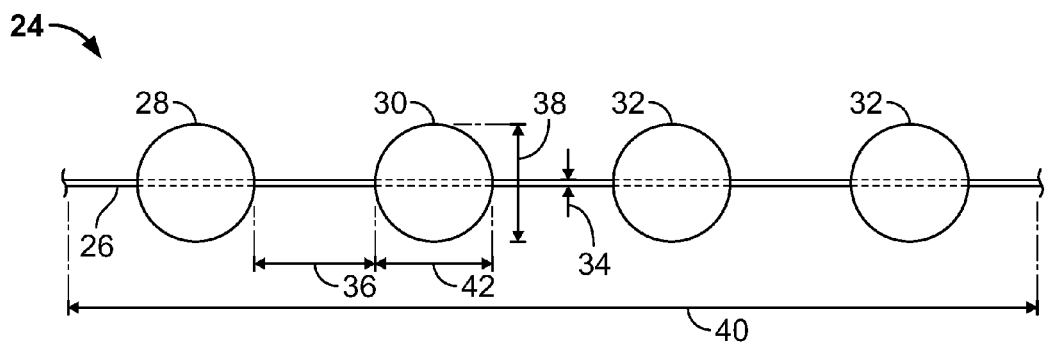
FIG. 3a illustrates an embodiment of the embolization device.
Figure 3B:
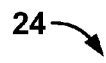

FIG. 3a illustrates an embodiment of a vascular embolization or occlusion device 24 having a flexible leader 26 that can be connected to a first non-expandable space-occupying element 28 and a second non-expandable space-occupying element 30. Additional non-expandable space-occupying elements 32 can also be connected to the leader 26 and provided in various lengths, depending on the typical volume of the sac 10 to be filled. The leader 26 can pass through the elements 28, 30 and 32. The leader 26 can be fixed to the elements 28, 30 and 32, or the elements 28, 30 and 32 can slide freely over the leader 26. As illustrated in FIG. 3b, the leader 26, even if secured within an element 28, 30, or 32, can flex and bend within each element 28, 30 or 32, or between the elements 28, 30 and 32.

The leader 26 can be a suture, preformed resilient structure, poppet, wire, fiber, monofilament, rail, or a woven thread or other combination thereof. The leader 26 can be completely separate and discrete from the elements 28, 30 and 32. The leader 26 can be made from polymer, for example polyester (e.g., DACRON® from E. I. du Pont de Nemours and Company, Wilmington, Del.), polypropylene, polytetrafluoroethylene (PTFE), expanded PTFE (ePTFE), nylon, casted and/or dehydrated (lyphilize-free dry) collagen, silicone, spunbound, non-woven, non-bioabsorbable polyester (e.g., REEMAY® from Reemay, Inc., Old Hickory, Tenn.) and combinations thereof. The leader 26 can have a leader diameter 34 from about 0.050 mm (0.0020 in.) to about 1.3 mm (0.050 in.), more narrowly from about 0.2 mm (0.006 in.) to about 0.25 mm (0.010 in.). A leader span 36 between the elements 28 and 30 can be from about 0 to about 2 times an element outer diameter 38, more narrowly from about 0.5 to about 1 time the element outer diameter 38. A total device length 40 from one end of the device 24 to the other can be any length desired, for example about 30 cm (1 ft.).

The elements 28, 30 and 32 can be spherical, cylindrical, or an approximation thereof. The elements 28, 30 and 32 can be made from any of the materials disclosed above for the leader 26 as well as collagen, glass, polylactic acid (PLA), poly(lactic-co-glycolic acid) (PLGA), polyglycolic acid (PGA), other bioabsorbable material, polyurethane, polyethylene, or metal, for example stainless steel, titanium or nitinol. The element outer diameter 38 can be more than about 0.1 mm (0.005 in.) of the leader diameter 34. The element outer diameter 38 can be larger than about 0.25 mm (0.010 in.) less than an inner diameter of a catheter through which the device 24 is deployed. The element outer diameter 38 can also be larger than about 2.0 mm (0.079 in.), more narrowly larger than about 2.7 mm (0.11 in.). An element length 42 can be in the aforementioned ranges for the element outer diameter 38.

A device volume can be determined by calculating the total volume of the elements 28, 30 and 32 added to the total volume of the leaders 26. If the leader 26 or the elements 28, 30 and 32 are made from bioabsorbable materials, the reduction of device volume over time can be accounted for when calculating device volume. The device volume can be from about 20 cc (1.2 in.$^3$) to about 200 cc (12.2 in.$^3$), more narrowly from about 60 cc (3.7 in.$^3$) to about 100 cc (6.1 in.$^3$).

FIGS. 4 and 5 illustrate an embodiment of the element 28 with the leader 26. The elements 30 and 32 can have embodiments identical to the element 28. The element 28 can be made from a first section 44 and a second section 46. The first section 44 can be secured to the second section 46. The sections 44 and 46 can have a section body 48 and an outer layer 50. The section body 48 can be solid, solid with one or more dimples or channels, or hollow. The outer layer 50 can be a porous membrane or have macroscopic holes or channels that are in communication with the section body 48. The element 28 can have one or more leader channels 52 having leader channel diameters 54 about equal to or greater than the leader diameter 34. The leader channels 52 can be fixed to the leader 26. Alternatively, the leader 26 can have a clearance with the leader channels 52. A ferrule 56 can be fixed to the leader 26. The ferrule 56 can be locked with an interference fit into a ferrule cavity 58.

FIGS. 6 and 7 illustrate an embodiment of the first section 44 and the element 28, respectively. FIGS. 8 and 9 illustrate another embodiment of the first section 44 and the element 28, respectively. In the embodiments shown in FIGS. 6-9, the sections 44 and 46 can be identically shaped. In the embodiments in FIGS. 4-7, the sections 44 and 46 can be shaped to fit the opposite section 44 or 46 and form an interference fit, for example a snap lock, with the opposite section 44 or 46. The interference fit minimizes movement of the sections 44 and 46 with respect to each other in any direction. In the embodiments in FIGS. 8 and 9, the sections 44 and 46 can be shaped to fit the opposite section 44 or 46 and form an interference fit that allows movement of the sections 44 and 46 with respect to each other in one translational direction.

Figure 10:
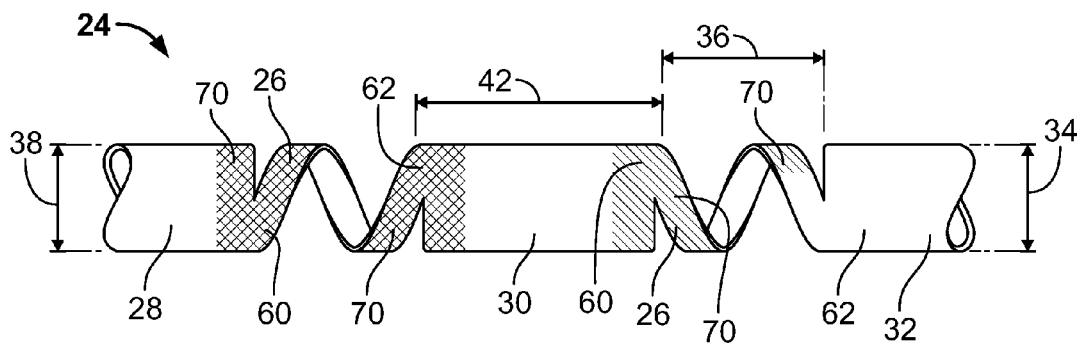
FIGS. 10 and 11 illustrate segments of embodiments of the embolization device.
Figure 11:
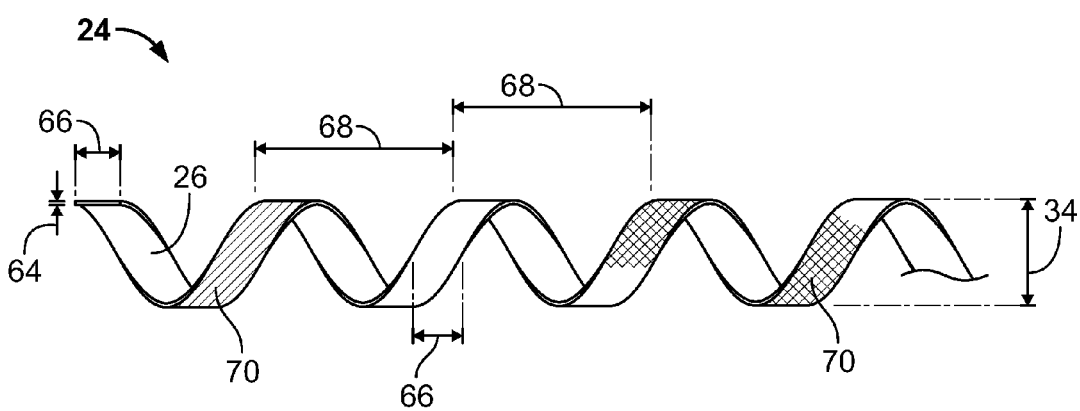

FIG. 10 illustrates a segment of an embodiment of the device 24 with the leaders 26 having first ends 60 and second ends 62 that can be integrated and conjoined segments of the elements 28, 30 and 32. A "segment" can be a portion or section of any part, a whole part, or groups of parts. A "segment" can be integral with or distinct from other parts. The leaders 26 can be preformed resilient structures formed into helical shapes. The device 24 can be made entirely from the leader 26 and without elements 28, 30 and 32, as illustrated in FIG. 11, or each element 28, 30 or 32 can be separated from the adjacent elements 28, 30 and 32 by as few as about 0.5 turns of the leader 26. More narrowly, each element 28, 30 or 32 can be separated from the adjacent elements 28, 30 and 32 by from about 2 turns to about 3 turns of the leader 26. The leaders 26 can have a preformed leader depth 64 from about 0.25 mm (0.0098 in.) to about 2.0 mm (0.079 in.), more narrowly from about 0.5 mm (0.02 in.) to about 1.0 mm (0.039 in.), and a preformed leader width 66 from about 0.5 mm (0.02 in.) to about 4.0 mm (0.16 in.), more narrowly from about 1.0 mm (0.039 in.) to about 2.0 mm (0.079 in.). The leaders 26 can also have wind lengths 68. The wind lengths 68 can be the longitudinal component of the length covered by about 360 degrees of helical turn in the element 28, 30 or 32. The wind lengths 68 can be about 2.0 mm (0.079 in.). The wind lengths 68 can also vary within a single element 28, 30 or 32, and five wind lengths 68 can be about 1.0 cm (0.39 in.).

The device 24 can be structurally reinforced. For example, a structural reinforcement 70 can be integrated onto the surface or encased by the leader 26 and/or the elements 28, 30, and 32. The reinforcement can be a binding agent, a polyester weave, or a coil or spiral element, for example a continuous wire wound within the device 24 such that the reinforcement 70 parallels the coils or helical shapes of the conjoined elements 28, 30 and 32 of the device 24.

Figure 12A:
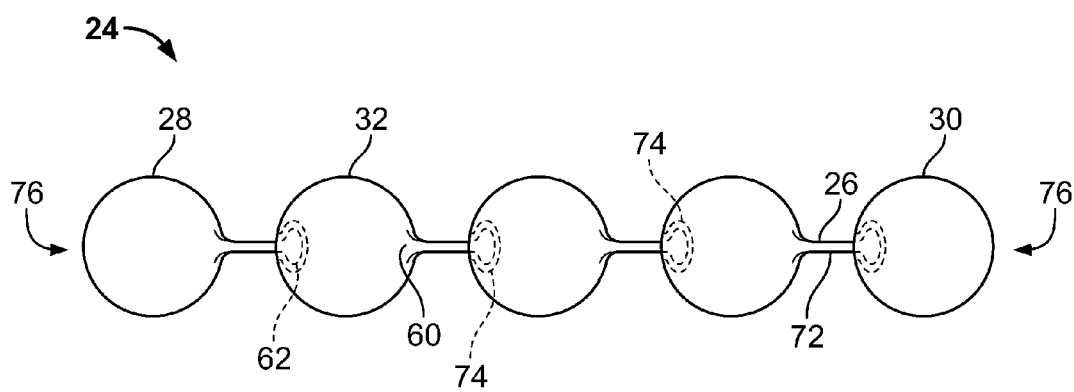
FIGS. 12a-c and 13 illustrate embodiments of the embolization device.
Figure 12B:
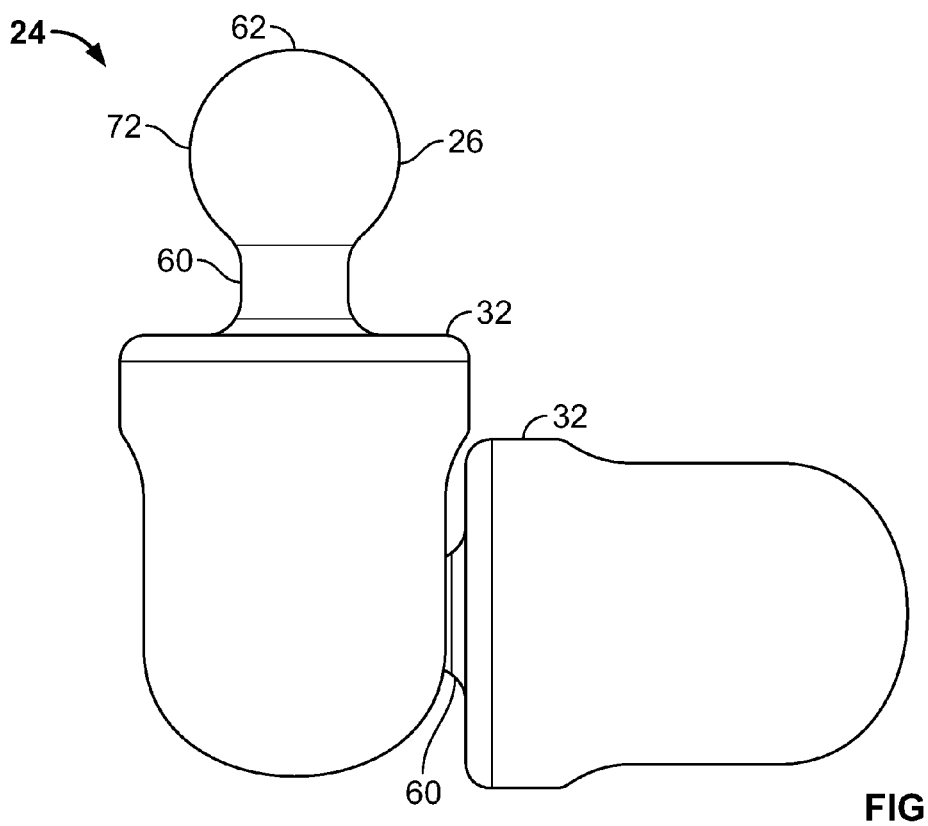
Figure 12C:
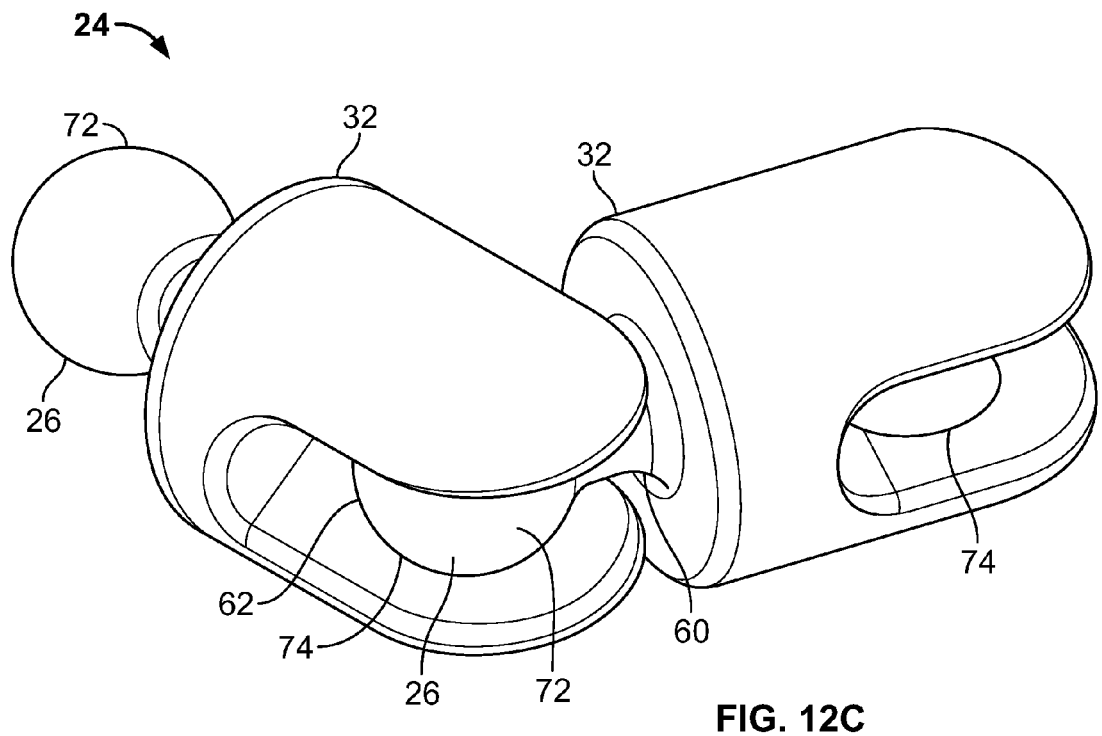

In other embodiments of the device 24 illustrated in FIGS. 12a-c, the leaders 26 can have a male interference-fit piece, for example brads or poppets 72, on a first end 60 of the leaders 26. The second ends 62 of the leaders 26 can be integrated and conjoined with the elements 28, 30 and 32. The elements 28, 30 and 32 can have female interference-fit pieces, for example plugs or sockets 74, integrated into the elements 28, 30 and 32 at the opposite ends of the elements 28, 30 and 32 from the poppets 74. A "piece" can be a leader, element, fiber, body, bladder, poppet or any other elements or group of elements or a segment of an element or groups of elements. The poppets 72 and sockets 74 can be shaped and sized to attach to each other with a sufficient interference fit to impede removal of the poppets 72 from the sockets 74. The elements 28 and 30 at open ends 76 of the device 24 do not attach to a neighboring element 28, 30 and 32. The elements 28 and 30 at the open ends 76 can lack the poppet 72 or the socket 74 on the open ends 76 of the elements 28 and 30.

Figure 13:
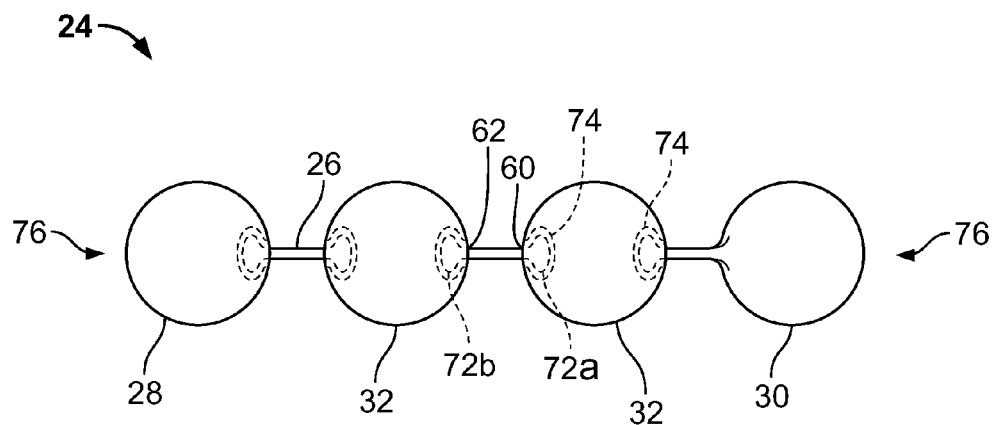

In another embodiment of the device 24 illustrated in FIG. 13, the first end 60 of the leader 26 can have a first male interference-fit piece, for example a first poppet 72a, and the second end 62 of the leader 26 can have a second male interference-fit piece, for example a second poppet 72b. A leader with male interference-fit pieces at two ends can be called a "dogbone". The elements 28, 30 and 32 can have two female interference-fit pieces, for example sockets 74, integrated into opposite ends of each element 28, 30 and 32.

Figure 14:
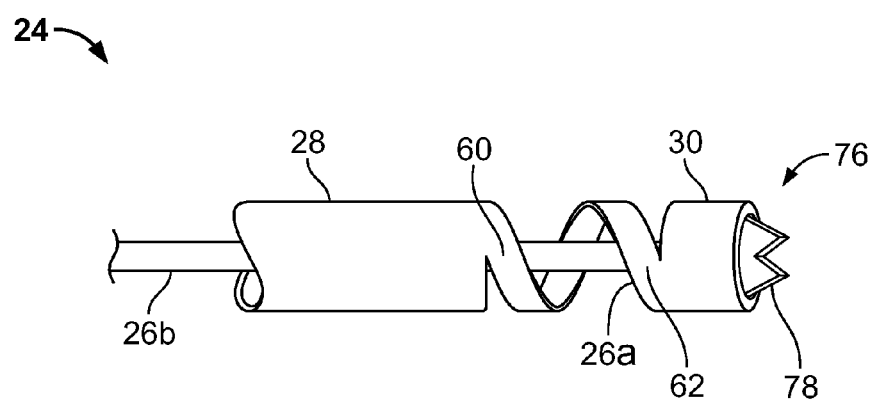
FIG. 14 illustrates a segment of an embodiment of the embolization device.

FIG. 14 illustrates a segment of an embodiment of the device 24 having first leaders 26a with ends 60 and 62 that can be integrated and conjoined segments of the elements 28 and 30 and a second leader 26b that can pass through the first leaders 26a and the elements 28 and 30. The second leader 26b can have an interference fit at one open end 76, for example a knot 78. The second leader 26b can be fixed or slidably attached to the elements 28 and 30.

Radiopaque materials known to one having ordinary skill in the art can be used anywhere in or on the device 24. Examples of radiopaque materials are barium, barium sulfate, titanium, stainless steel, nickel-titanium alloys (e.g., NiTi), and gold. The ferrule 56 can be made from radiopaque materials. A radiopaque patch or contrast agent can also be integrated into or placed on the leader 26 or the elements 28, 30, and 32. The contrast agent can be permanent or can be adapted to extravagate over time post-implantation. A radiopaque fiber can be wound integrally with the leader 26.

The radiopaque element can be present in a quantity sufficient to allow the operator to view deployment of the device 24 upon delivery, but not sufficient to obstruct the visualization of adjacent tissues and structures post-implantation. For example, upon deployment, the operator can visualize the initial placement and nesting of the elements 28, 29 and 30 and/or the leader 26, but post-implantation the visualization of the prosthesis 8 can be unobstructed by the radiopaque nature of the elements 28, 29 and 30 and/or the leader 26.

The elements 28, 30 or 32 can be filled or coated with an agent delivery matrix known to one having ordinary skill in the art and/or a therapeutic and/or diagnostic agent and/or a binding agent. The device 24, or any of the parts of the device 24, can be coated with the agents. These agents can include radioactive materials; radiopaque materials, for example gold; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 and 2 (COX-1 and COX-2) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 specific inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of agents can also include gel, for example, hydrogel, xerogel, aerogel, gelatin (e.g., bovine-derived gelatin), agar, sugars and combinations thereof. Examples of other agents are provided in Walton et al, Inhibition of Prostoglandin $E_2$ Synthesis in Abdominal Aortic Aneurysms, *Circulation*, Jul. 6, 1999, 48-54; Tambiah et al, Provocation of Experimental Aortic Inflammation Mediators and Chlamydia Pneumoniae, *Brit. J. Surgery* 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Sp1 Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties. Binding agents can include any of the aforementioned agents suitable for binding and a polyester weave, a coil or spiral element, a net, or other mesh, or a combination thereof. Once the device 24 is deployed, these agents can provide various benefits such as i) promoting fusing of the space-occupying elements 28, 30 or 32 to each other or to the surrounding biologic materials (e.g., a collagen coating), and/or ii) promoting a thrombogenic response within the sac 10 to stabilize the device 24 and the prosthesis 8, and/or iii) promoting healing of the aneurysm at the cellular level such as in the case of treating an inflammatory response, and/or iv) controlling the flexibility of the device 24.

Figure 15:
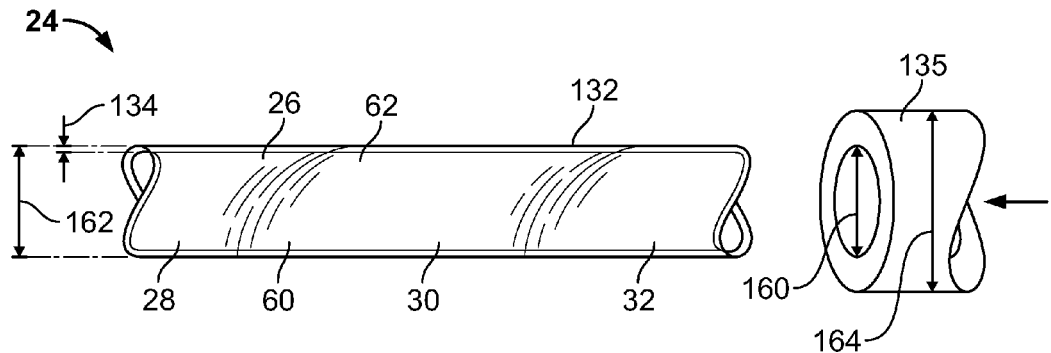
FIGS. 15, 16a and 16b illustrate segments of embodiments of the embolization device.

FIG. 15 illustrates a segment of an embodiment of the device 24 that can be similar to the embodiment illustrated in FIG. 10 or 11. The device 24 can be coated with a binding agent 132. (The binding agent 132 is transparent with outlines for illustrative purposes in FIGS. 15, 16a and 16b).

The device 24 can be substantially fully longitudinally compressed before being coated and, for example, held in a cylindrical configuration by the binding agent 132. The device 24 can be placed over a wire, mandrel and/or a delivery catheter (not shown). While in a compressed configuration, portions of the device 24 can also overlap the device 24, itself. The binding agent 132 can be any agent listed above or combinations thereof. The binding agent 132 can have a binding agent thickness 134 from about 0.01 mm (0.0005 in.) to about 1.3 mm (0.050 in.), for example, about 0.25 mm (0.010 in.). The binding agent 132 can be in a substantially solid form before use. The binding agent 132 can transitionally decrease the flexibility of the device 24 during deployment. The binding agent 132 can increase the column strength of the device 24, thereby enhancing the pushability of the device 24 by a hollow pusher rod or ramming catheter 135.

The binding agent 132 can cover the seams of the leader 26, as shown by the binding agent on the leader 26 between the first and second elements 28 and 30. The binding agent 132 can also expose the seams of the leader 26, as shown by the leader 26 between the second and third elements 30 and 32.

A first device can also be placed against a longitudinal end of a second device, forming a butt joint. The butt joint can be covered in the binding agent 132. The first and devices can therefore be constrained to each other at the butt joint.

Figure 16A:
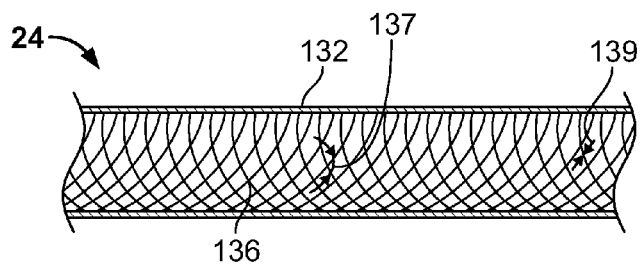
Figure 16B:
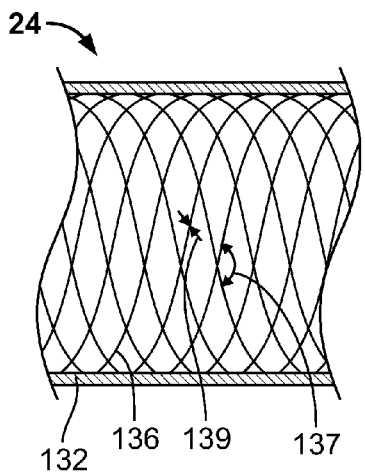

FIGS. 16*a* and 16*b* illustrate a segment of an embodiment of the device 24 that can be woven from fibers 136. The fibers 136 can be woven into a cylindrical configuration and coated with the binding agent 132. The fibers 136 can be made from any of the materials listed for the leader 26 or the elements 28, 30 and 32 or any combination thereof. The fibers 136 can have a fiber pitch 137 from about 45° to about 80°. FIG. 16*a* illustrates the device 24 in a first state that can have a smaller fiber pitch 137 than the device 24 in a second state illustrated in FIG. 16*b*. Due to a coating of the binding agent 132, the device 24 can be held at a pre-selected fiber pitch 137 during all or part of use (e.g., during deployment). The fibers 136 can have a fiber diameter 139 from about 0.03 mm (0.001 in.) to about 1.0 mm (0.04 in.), more narrowly from about 0.1 mm (0.005 in.) to about 0.25 mm (0.010 in.).

Figure 17:
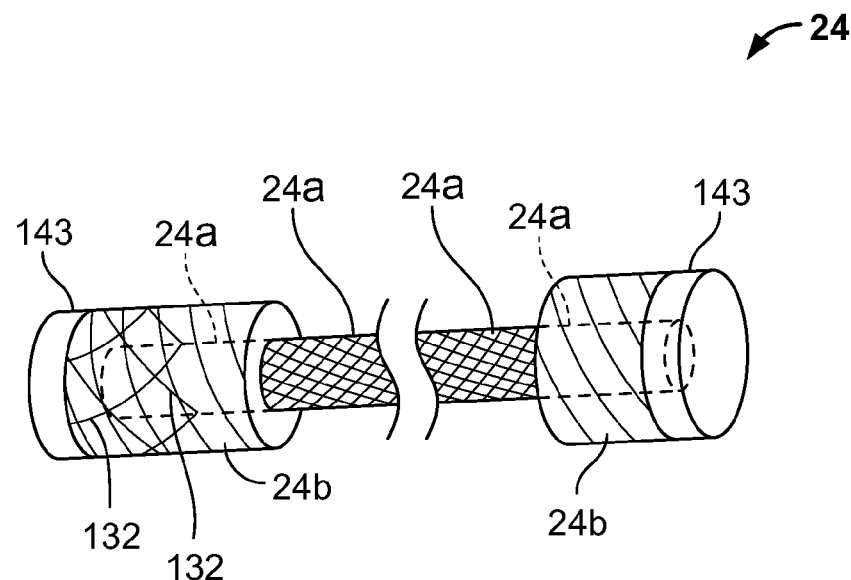
FIG. 17 illustrates a partial cut-away view of an embodiment of the embolization device.

FIG. 17 illustrates an embodiment of the device 24 that can have a combination of the above embodiments in alternating states of tension and compression to minimize or completely prevent longitudinal expansion of the device 24. A first sub-device 24*a*, for example the woven embodiment of the device 24 illustrated in FIG. 16*a* or 16*b*, with or without the binding agent 132, can be radially surrounded by a second sub-device 24*b* (shown as a cut-away view for illustrative purposes), for example the helical embodiment of the device 24 illustrated in FIG. 11. The second sub-device 24*b* can be radially surrounded by a binding agent 132, for example a radial constraining device such as a net (shown only at one end of the device 24 and as a cut-away view for illustrative purposes).

The first and second sub-devices 24*a* and 24*b* and the constraining device 141 can be fixedly attached at both longitudinal ends to end caps 143. The first sub-device 24*a* can be in tension when fixedly attached to the end caps 143. The second sub-device 24*b* can be in compression when fixedly attached to the end caps 143. The orientation of the tension and compression of the first and second sub-devices 24*a* and 24*b* can be reversed.

Figure 18:
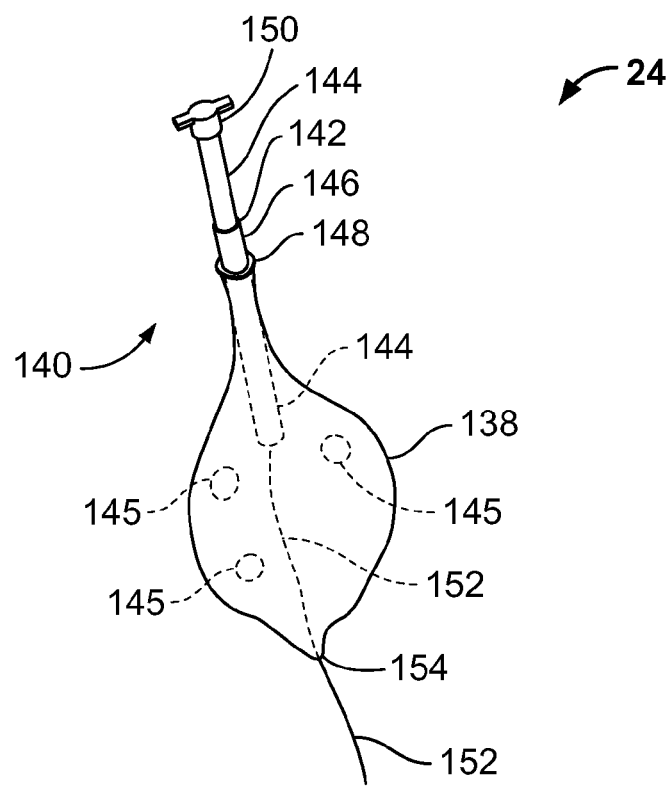
FIGS. 18 and 19 illustrate embodiments of the embolization device.

FIG. 18 illustrates an embodiment of the device 24. The device 24 can have a body 138 that can have a fillable bladder, for example a woven, knit or doubleknit polyester fabric bag. The body 138 can be sized and shaped to fit a specific sac 10, for example, based on visualization data from a visualization tool used before the device 24 is deployed. Alternatively or in conjunction with the aforementioned sizing and shaping, numerous, small, discrete devices 24 (e.g., bodies 138) can be used to fill a specific sac 10. The device 24 can be large enough to minimize the risk that after the device is deployed that the device 24 might pass into the bloodstream and become an embolus, but optionally fillable with particles 145 that could otherwise be small enough to embolize.

The fillable bladder and the body 138 can be the same or different elements. The body 138 and/or the bladder can be made from any material listed above for the leader 26, the elements 28, 30 or 32 or any combination thereof. The body 138 and/or the bladder can be permeable to body fluids and/or a filling agent. The body 138 can have very fine pores. The body 138 can have a proximal port 142 at a proximal end 140 of the body 138. A filler tube 144 can be placed in the proximal port 142 and provide access to the inside of the bladder and/or the body 138. At the proximal end 140, the body 138 can have a neck 146. The neck 146 can have a seal 148, for example a sealing band or valve. When closed, the seal 148 can be substantially fluid-tight or the seal 148 can be less than about 8 mm (0.3 in.) diameter. The proximal end of the filler tube 140 can be attached to a syringe connecter 150, for example, a syringe port or connector known to one having ordinary skill in the art. A guidewire 152 can pass into the proximal end 140 of the body 138. The guidewire 152 can pass out of the body 138 at the guidewire port 154 to allow delivery of the bladder from an over-the-wire catheter. The guidewire port 154 can form a substantially fluid-tight seal with the body 138. The device 24 can also be used without the guidewire 152, and the guidewire port 154 can be absent in the device 24.

The body 138 and/or the bladder can contain the filling agent. The body 138 and/or the bladder can be pre-filled with the filling agent or injected with the filling agent as described above. The filling agent can be in the form of particulates, for example, pellets, pieces, chunks, chips, powder, fluid, gel or a combination thereof. The filling agent can be made from any material listed for the agent, the leader 26 the element 28, 30 or 32 or combinations thereof. The filling agent can be larger than any openings on the body 138 during use (e.g., pores, ports, or seals) to minimize the filling agent exiting the body 138 and entering the bloodstream.

Figure 19:
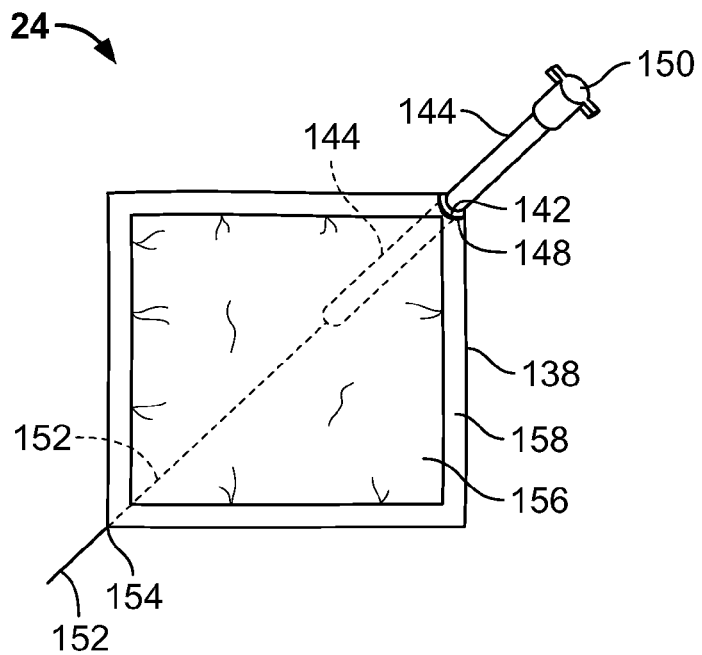

FIG. 19 illustrates an embodiment of the device 24 similar to the embodiment of the device 18 illustrated in FIG. 18. The device 24 can have a body 138 that can have a fillable bladder 156. The body 138 can also have a bladder seal 158 substantially around the perimeter of the body 138. The bladder seal 158 can be, for example, a glue, heat or stitch seal. The body 138 can have various geometric configurations including a substantially square, rectangular, semi-elliptical (e.g., hemi-elliptical), elliptical, semi-circular (e.g., hemi-circular), circular, oblong, or totally irregular shape. The shape of the body 138 can promote the body 138 to conform with the sac 10 morphology to increase the thrombogenicity in the sac 10, while the shape of the body 138 can still encourage containment of the body 138 within the sac 10 to minimize risk of the body 138 becoming an embolus in the bloodstream. The proximal port 142 can be in the corner or the side of the bladder seal, or orthogonally out of the face of the bladder 156.

Method of Making

The elements 28, 30 and 32 and the leader 26 can be made from methods known to those having ordinary skill in the art. For example, the elements 28, 30 and 32 can be molded or machined. The embodiments of the device 24 illustrated in FIGS. 10, 11, 14 and/or 15 can be extruded and then a helical cut in the extrusion can be made by a blade, laser, water jet or hot wire to form the leaders 26 and 26*a*.

The elements 28, 30 and 32 can be molded, machined, or mounted onto the leader 26. The elements 28, 30 and 32 can be mounted to the leader 26 with an interference fit, for example by tying knots in the leader 26 surrounding the elements 28, 30 and 32 mounting the elements 28, 30 and 32 onto the ferrule 56 which is already crimped onto the leader 26. The elements 28, 30 and 32 can be pressure fitted onto the leader 26, for example by crimping the elements 28, 30 and 32 onto the leader 26, snapping snap-together sections 44 and 46 onto the leader 26, or distortion mounting by heating the elements 28, 30 and 32 to a threshold of thermal distortion. The elements 28, 30 and 32 can be glued onto the leader 26 with a biocompatible adhesive (e.g., cyanoacrylate); bonded ultrasonically; or heat bonded (e.g., melting, heat welding). Each section 44 or 46 can be attached to the other section 44 or 46 with any of the above methods.

Any part of the device 24, or the device 24 as a whole after assembly, can be coated by dip-coating or spray-coating methods known to one having ordinary skill in the art. One example of a method used to coat a medical device for vascular use is provided in U.S. Pat. No. 6,358,556 by Ding et al. and hereby incorporated by reference in its entirety. Time release coating methods known to one having ordinary skill in the art can also be used to delay the release of an agent in the coating, for example inclusion of a collagen matrix in the coating.

The device 24 can be coated with the binding agent 132 while the leader 26 is in a closed position, as shown by the binding agent on the leader 26 between the first and second elements 28 and 30 in FIG. 15. The device 24 can be coated with the binding agent 132 while the leader 26 is in an opened position, as shown by the binding agent on the leader 26 between the second and third elements 30 and 32 in FIG. 15. Depending on the relaxed state of the leader 26, the leader 26 can be opened and/or closed by twisting, necking, compressing or extending.

Method of Use

Before using the device 24, the sac 10 can be cleaned of debris (e.g., thrombi), for example, by mechanically macerating the debris or using a lytic agent (e.g., Urokinase, for example Abbokinase® from Abbott Laboratories, Abbott Park, Ill.). Examples of devices capable of performing pharmomechanical treatment—that can be delivered to the sac 10 through the same delivery apparatus as the device 24—are the TRELLIS™ and FINO™ from Bacchus Vascular, Inc. (Santa Clara, Calif.). Use of the device 24 can be performed while using a visualization tool, for example fluoroscopy or computed tomography (CT) scanning. The volume of the sac 10 not filled by debris can be estimated from visual inspection, for example by inspection of images from the visualization tool. Software known to one having ordinary skill in the art can also be used to assist in estimating the volume of the sac 10.

A length of the device 24 can be stored in a sterile package, for example by an individual predetermined length, or on a spool, spindle, or in a cartridge. The device volume can be reduced by removing more than enough of the device 24 from the sterile package and then reducing the length of the device 24, for example, by cutting the leader 26 or unplugging a poppet 72 from a socket 74. In this way, the device volume can be reduced to the approximate volume of the sac 10 not filled by debris. The device volume can be large enough to substantially fill the vascular site, and the device volume can be small enough to prevent substantial alteration of the natural fluid flow through the prosthesis 8.

Figure 20:
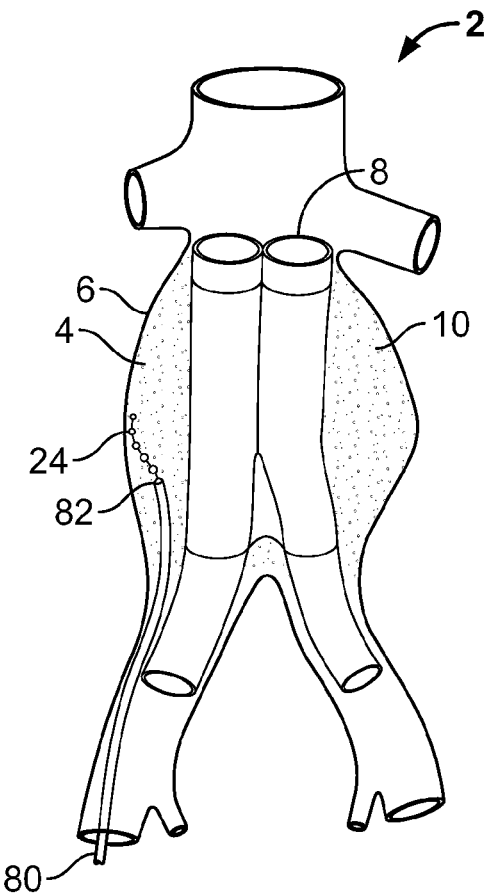
FIG. 20 illustrates an embodiment of the method of implanting the embolization device.

The device 24 can be deployed to the sac 10 using a trans-graft, trans-collateral, trans-sac, or endoluminal procedure. As illustrated in FIG. 20, a catheter 80 with a distal exit 82 can be placed in the aneurysm 4. The distal exit 82 can be placed at the sac 10. The device 24 can then be passed through the catheter 80 and distal exit 82, and the device 24 can be deployed into the sac 10.

Figure 21:
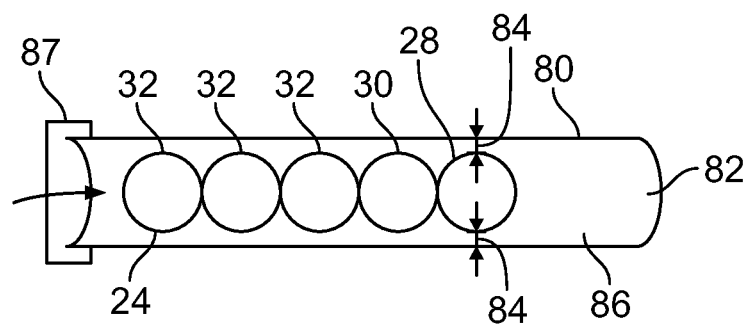
FIG. 21 is a cut-away view of a catheter carrying an embodiment of the embolization device.

As illustrated in FIG. 21, a catheter clearance 84 is the distance between the device 24 and an inner wall 86 of the catheter 80. The inner walls 86 of the catheter 80 can act as a guide for the device 24 during deployment. If the catheter clearance 84 is too large, the inner walls 86 of the catheter 80 can no longer act as a guide and the device 24 can "boxcar" within the catheter 80. Boxcarring occurs when the elements 28, 30 and 32 bunch up and impair delivery, preventing an upstream element from transmitting force to a downstream element in a direction substantially parallel with the inner walls 86. The maximum catheter clearance 84 before the elements 28, 30 and 32 can begin to boxcar is the "critical clearance". The critical clearance can be about 80% of the element outer diameter 38, more narrowly about 26% of the element outer diameter, yet more narrowly about 12% of the element outer diameter 38.

As illustrates in FIG. 15, the device 24 can be propelled during deployment by pushing (as shown by the arrow) the device 24 with the pushing rod or ramming catheter 135. The ramming catheter 135 can have an inner diameter 160 smaller than the outer diameter 162 of the device 24. The ramming catheter 135 can have an outer diameter 164 larger than the outer diameter 162 of the device 24.

If the device 24 is coated with a binding agent 132, the device 24 can have an increased column strength and a decreased flexibility before use and during passage through the catheter 80. The binding agent 132 can be exposed to a softening agent during use. The softening agent can soften the binding agent 132 and can increase the flexibility of the device 24 during use.

While the device 24 is passed through the catheter 80, the device 24 can be substantially separated from the softening agent. The device 24 can be exposed to the softening agent when the device 24 exits the distal exit 82 and is placed in the aneurysm 4. Softening agents can be blood, other body fluids, other agents known to one having ordinary skill in the art, or combinations thereof. Softening agents can be injected through the catheter 80 at the time of deployment, thereby exposing the device 24 to the softening agents within the catheter 80 so the device becomes more flexible as the device 24 exits the catheter 80.

An end of the catheter 80 can have a valve 87 to minimize or completely prevent backflow of body fluids or other leakage and improve the connection of other devices to the end of the catheter 80. Use of the valve 87 at the end of the catheter 80 is understood to one having ordinary skill in the art. The valve 87 can be, for example, a hemostasis valve (e.g., from Cook, Inc., Bloomington, Ind.).

A method of deploying the device 24 illustrated in FIG. 18 or 19 can include deflating the body 138 and/or the bladder 156 (for ease of description, hereafter referred to collectively as the body 138) to place the device 24 into the catheter 80. The filler tube 144 and/or syringe connector 150 can be attached to the body 138 before or during the procedure. The seal 148 can be partially closed to seal around the filler tube 144. The body 138 can be passed through a catheter and positioned in the sac 10. The guidewire 152 can be used to direct the body 138.

Once in a desired position in the sac 10, the guidewire 152 can be removed from the body 138. A syringe or catheter can be attached in fluid communication to the filler tube 144 and/or syringe connector 150. The body 138 can then be filled with a particulate, a flowable material under pressure, or a combination thereof. The particulate can be an expandable material. The particulate can expand, for example, when exposed to body fluids. The flowable material can be a solidifying agent, for example, a gel, stereolithography polymers, a recently-prepared fast setting polymer, or a combination thereof. The body 138 can be pre-filled (e.g., filled before deployment of the body 138 into the sac 10). The body can be filled by a combination of pre-filling and filling after the deployment of the body 138 into the sac 10.

When the body 138 is filled to a desired size and shape, the flow of flowable material can be stopped. The flowable material can then be caused to harden or solidify, for example, by exposure to a second material, heating, cooling, exposure to RF radiation (e.g., UV light), time exposure, or a combination thereof. The filler tube 144 can be removed from the body 138 and the seal 148 can be fully sealed. Any amount of the flowable material can also exit the body 138 by the pores in the body 138. The flowable material can have an agent for example, any of the therapeutic agents, diagnostic agents, radiopaque agents or binding agents listed above, or combinations thereof.

Figure 22:
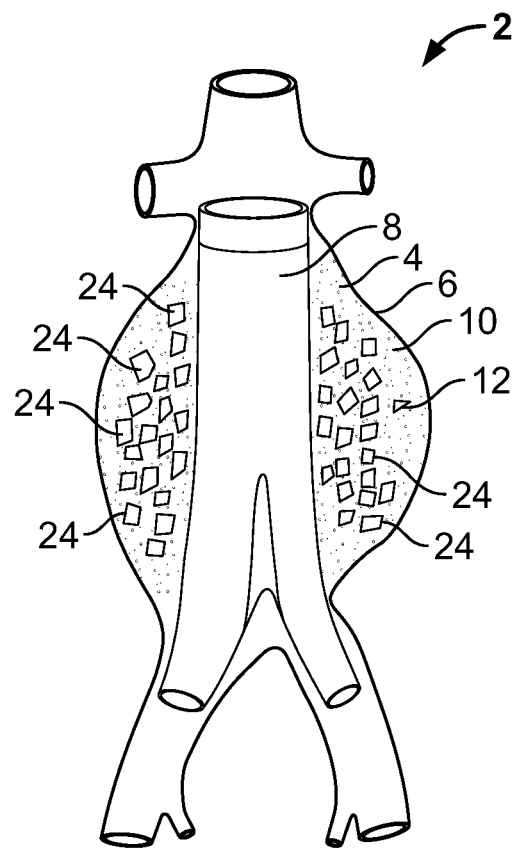
FIG. 22 illustrates an embodiment of the method of implanting the embolization device.

FIG. 22 illustrates a method of deploying multiple devices 24 to the sac 10. The devices 24 can be finable, for example the embodiments shown in FIG. 18 or 19. The devices 24 can be small enough to fit multiple devices 24 into the sac 10. The devices 24 can be deployed using a delivery catheter known to one having ordinary skill in the art with or without the guidewire 152.

Figure 23:
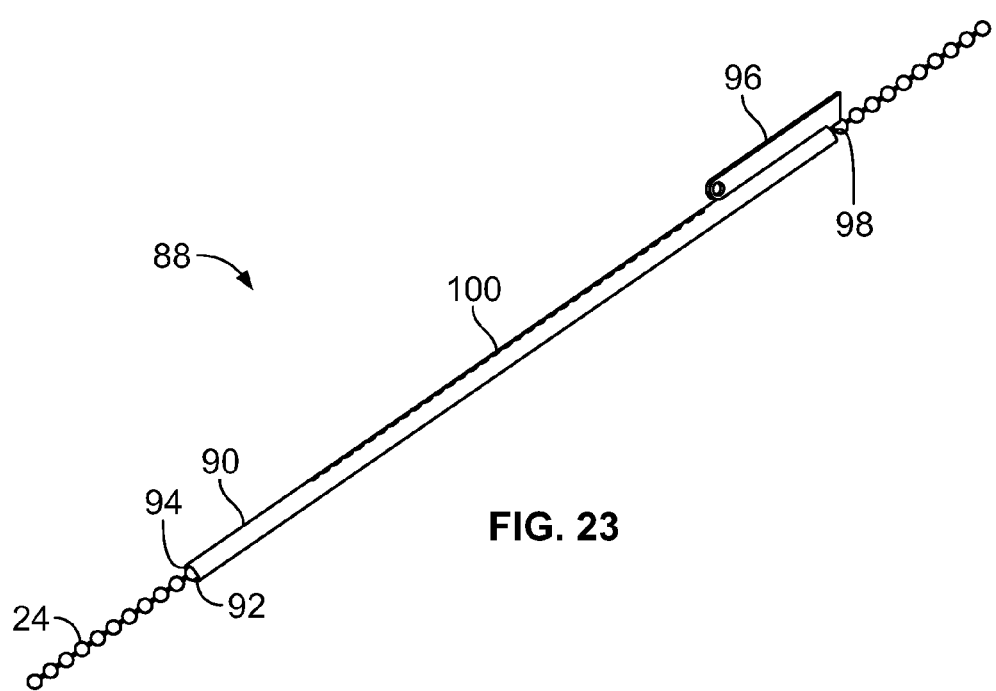
FIGS. 23 and 24 illustrate embodiments for the drivers used to deploy the embolization device.

FIG. 23 illustrates a ratcheting driver 88 having a feed tube 90 that can be used to control the device 24 during deployment. The device 24 can pass through a channel 92 in the feed tube 90. An end 94 of the feed tube 90 can connect to the valve 87 or the catheter 80. The driver 88 can have a spring-loaded handle 96. The handle 96 can be connected to a ram 98. The handle 96 can move along a track 100 in the feed tube 90. When the handle 96 is pushed, the ram 98 can press the device 24 forward through the channel 92. When the handle 96 is released, the handle 96 can revert to a starting position and prevent the device 24 from moving backwards through the channel 92.

Figure 24:
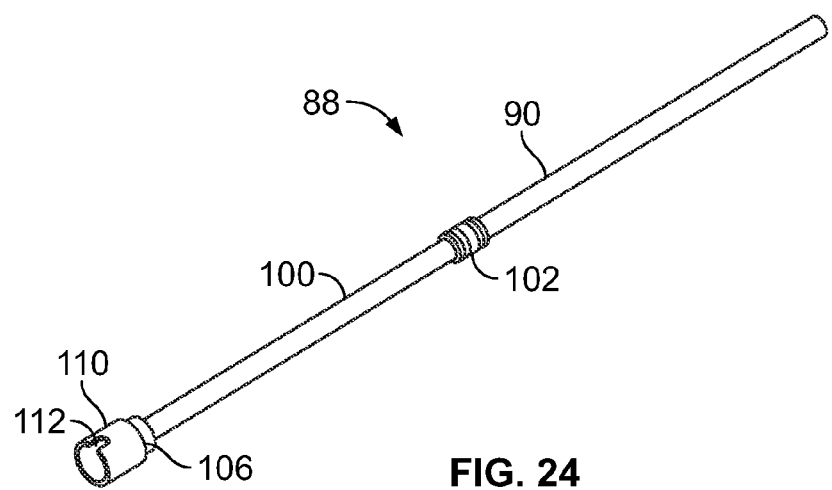
Figure 25:
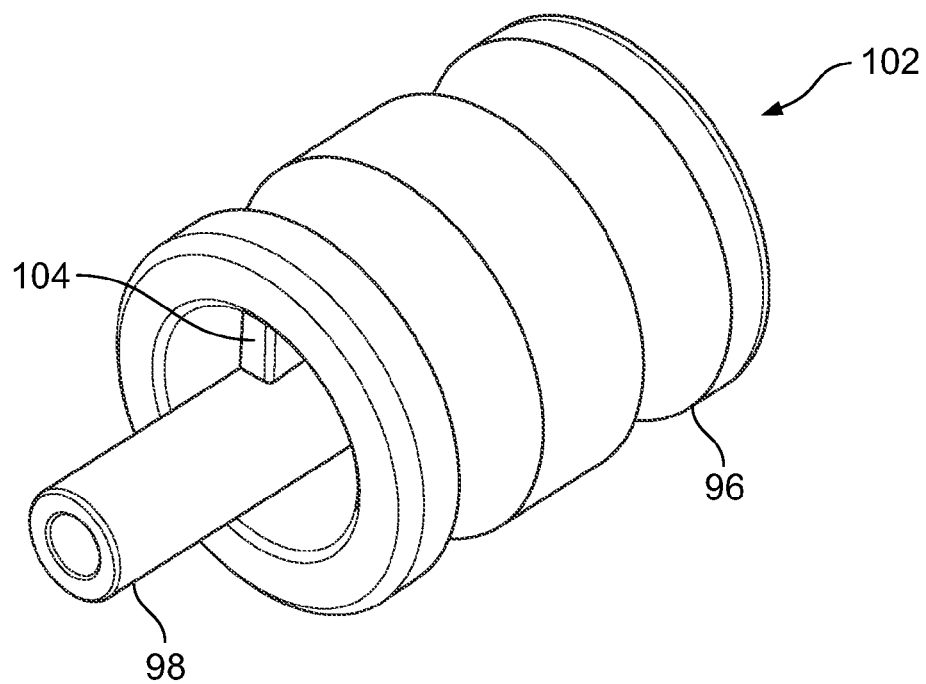
FIG. 25 illustrates an embodiment of the slider from the driver.

FIG. 24 illustrates a sliding driver 88 having a slider 102. The slider 102, illustrated in FIG. 25, can have a rib 104 that can engage the track 100. The slider 102 can abut and deliver a force to the end of the device 24 when the device 24 is in the channel 92.

The geometries of the elements 28, 30 and 32 of the device 24 and the properties of the leader 26 can benefit delivery of the device 24. As the slider 102 delivers force to the end of the device 24, the leader 26 can buckle or flex, allowing elements 28, 30 and 32 to approximate and transmit force from one element 28, 30 or 32 to the other elements 28, 30 or 32, thereby giving the device 24 sufficient column strength to move through the channel 92.

Figure 26:
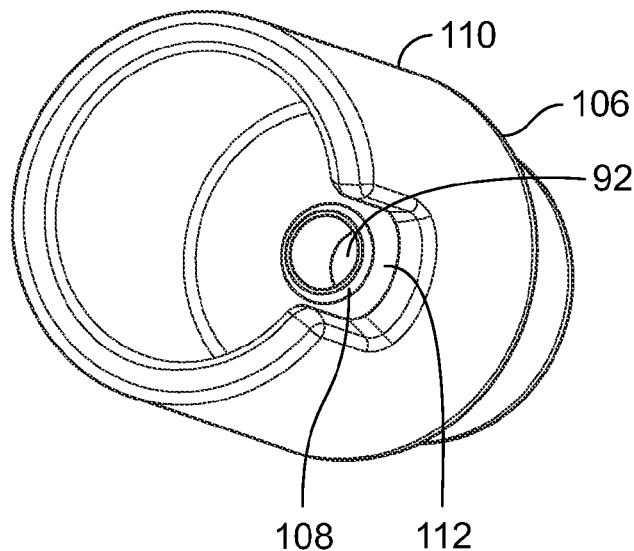
FIG. 26 illustrates an embodiment of the connector.
Figure 27:
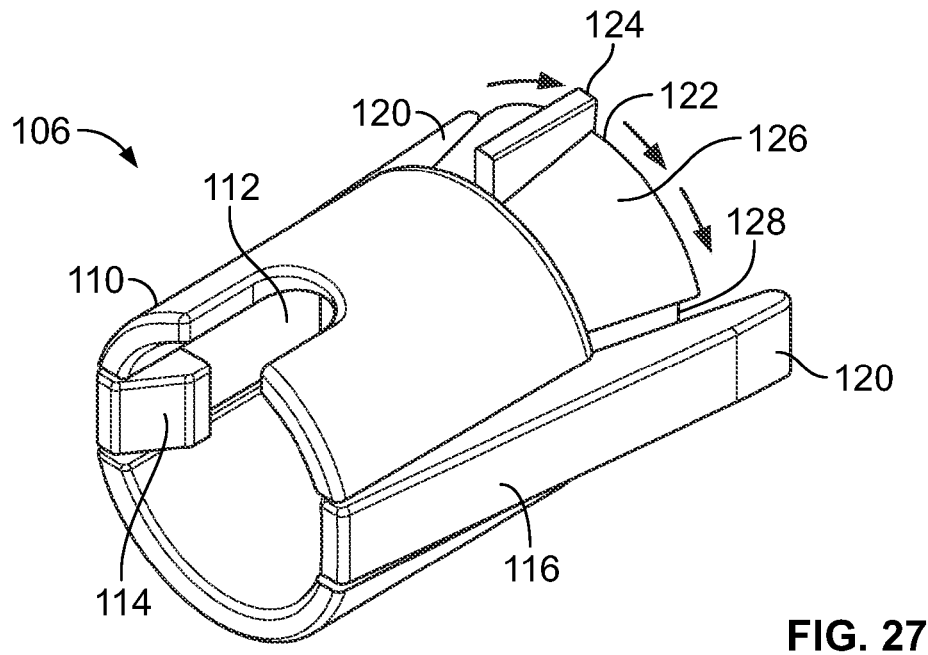
FIG. 27 illustrates an embodiment of the connector in an unlocked configuration.
Figure 28:
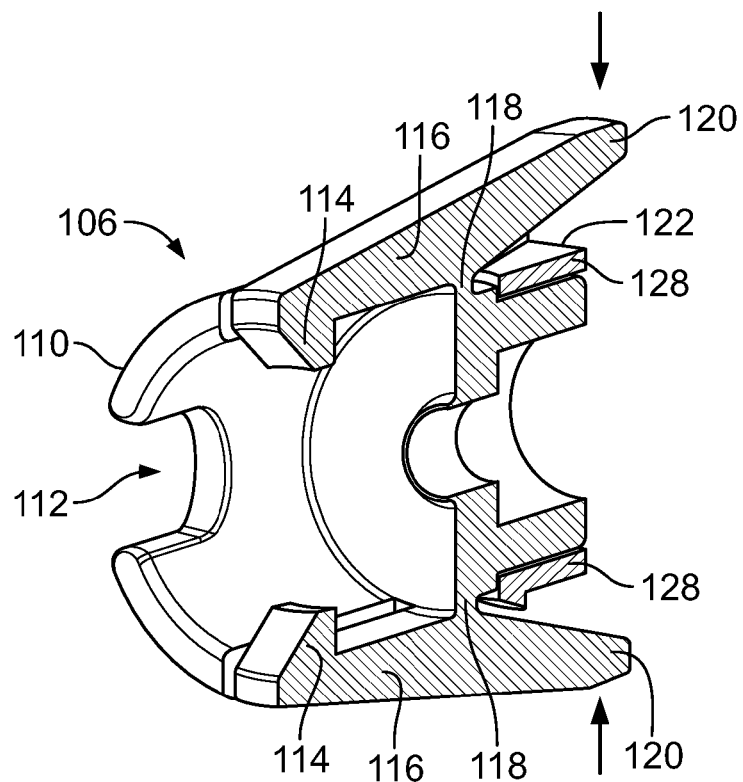
FIG. 28 is a cross-sectional view of the connector of FIG. 27.
Figure 29:
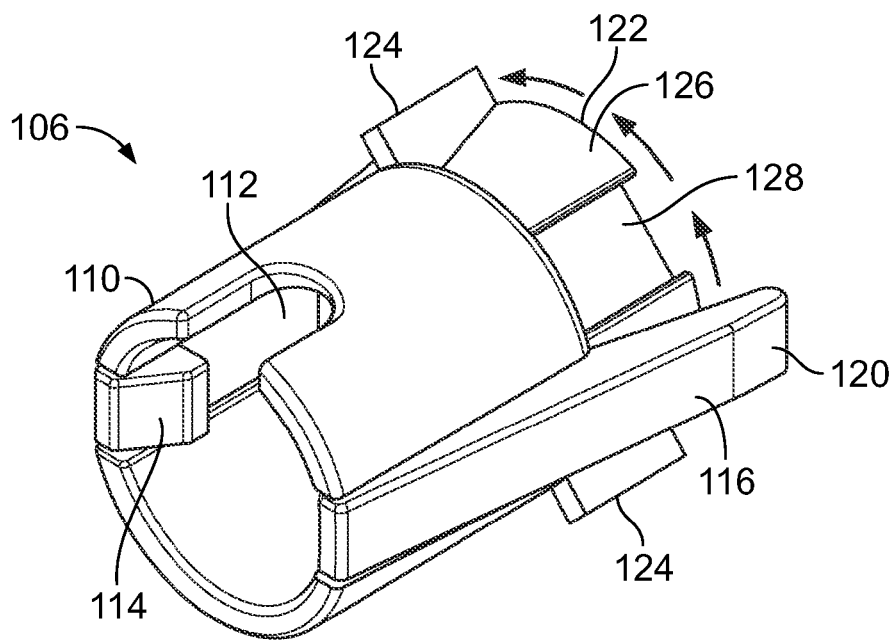
FIG. 29 illustrates the connector of FIG. 27 in a locked configuration.
Figure 30:
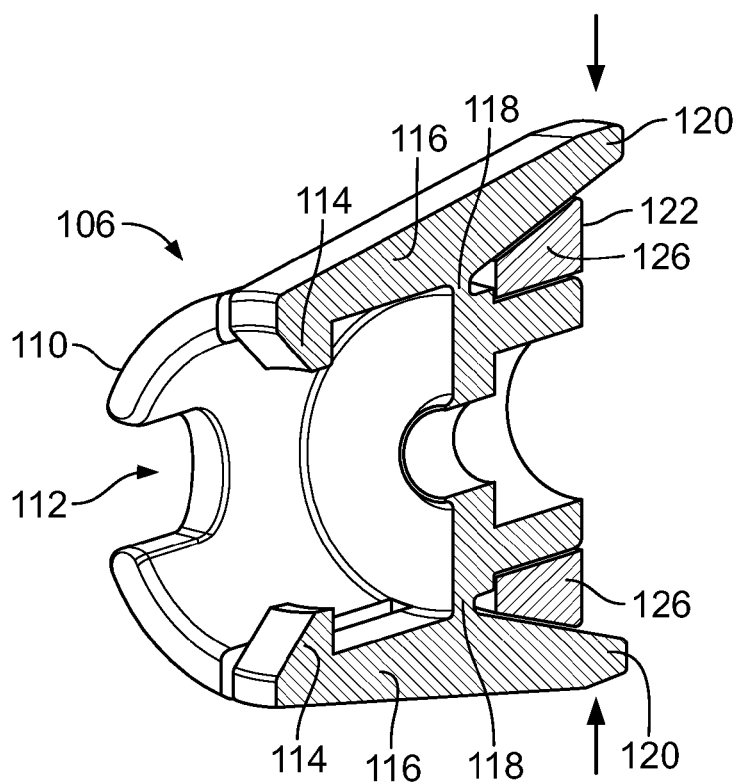
FIG. 30 is a cross-sectional view of the connector of FIG. 29.

As illustrated in FIG. 26, a connector 106 at the end 94 of the feed tube 90 can have a lipped hub 108 and a collar 110. The lipped hub 108 can feed into the valve 87 or the opening of a channel in the catheter 80. The collar 110 can fit over the valve 87 or the end of the catheter 80 that joins with the feed tube 90, or the collar 110 can join with another intermediary device between the catheter 80 or the valve 87 and the feed tube 90. The connector 106 can have a check port 112 in the collar 110.

FIGS. 27-30 illustrate an embodiment of the connector 106 that can lock to, and unlock from, the catheter 80. A first end of the connector 106 can have a latch 114 that can form a friction or interference fit with the valve 87 or the catheter 80 (not shown) when the valve 87 or the catheter 80 is loaded into the collar 110 past the latches 114. The latches 114 can be rigidly attached to lever arms 116. The lever arms 116 can be attached to the connector 106 at an attachment location 118 so that the position of the lever arms 114 forces the latches 114 to form the friction or interference fit with the valve 87 or the catheter 80 when no external forces are applied to the lever arms 116. A second end of the lever arm 116 can also have a press tab or button 120.

When a force (shown by arrows in FIG. 28) is applied to the buttons 120, the lever arms 116 can rotate around the attachment location 118, removing the friction or interference fit between the latches 114 and the valve 87 or the catheter 80.

The connector 106 can have a lock 122 that can be rotatably attached to the remainder of the connector 106. Tabs 124 can protrude from the lock 122. The tabs 124 can be used to aid rotation (shown by arrows in FIGS. 27 and 29) of the lock 122 relative to the remainder of the connector 106, and to provide an interference fit to prevent the lock 122 from turning from one lever arm 114 past the next lever arm 114. The lock 122 can have a thick portion 126 and a thin portion 128.

The lock 122 can be rotated to position the thick portion 126 between the lever arms 116 and a retaining wall 130 (shown in FIGS. 29 and 30), minimizing the rotation of the lever arms 116 and preventing the removal of the friction or interference fit between the latches 114 and the valve 87 or the catheter 80. With the lock 122 in this position, the valve 87 or the catheter 80 can be locked to the connector 106.

The lock 122 can be rotated to position the thin portion 128 between the lever arms 116 and the retaining wall 130 (shown in FIGS. 27 and 28), allowing substantially free rotation of the lever arms 116 and enabling removal of the friction or interference fit between the latches 114 and the valve 87 or the catheter 80. With the lock 122 in this position, the valve 87 or the catheter 80 can be unlocked and removed from the connector 106.

The driver 88 can be integrated with the sterile package (e.g., individual predetermined length, spool, spindle, or cartridge) loaded with the device 24. A new package loaded with the device 24 can replace or be swapped for an old package at the connector 106.

The device 24 can be visualized by the visualization tool before, during and after the device 24 has been deployed. After the device 24 has been deployed, any agents in or on the device 24 can elute into the tissue and fluids. The vascular prosthetic 8 can be implanted before, during or after the device 24 is deployed.

It is apparent to one skilled in the art that various changes and modifications can be made to this disclosure, and equivalents employed, without departing from the spirit and scope of the invention.

We claim:
1. A method of filling an aneurysm space within the abdominal aorta, the method comprising:
placing a prosthesis in the abdominal aorta of a subject;
delivering a fillable bladder in a deflated state into the aneurysm space using a catheter;

placing a filler tube in fluid communication with a single inflow port of the fillable bladder, wherein the filler tube provides access to an interior of the fillable bladder, and wherein the fillable bladder comprises a bladder seal surrounding the fillable bladder, wherein the bladder seal has a first side, a second side, a third side, and a fourth side, wherein a segment of the first side is parallel to a segment of the second side, wherein a segment of the third side is parallel to a segment of the fourth side, and wherein the segment of the first side is perpendicular to the segment of the third side;

filling the fillable bladder with a filling agent through the filler tube until the fillable bladder reaches a desired size in the aneurysm space, wherein the desired size is a size which prevents dislodgment of the prosthesis and allows natural fluid flow through the prosthesis placed in the abdominal aorta and the filling agent comprises at least one of a particulate and a flowable material;

hardening the filling agent;

removing the filler tube from the fillable bladder; and sealing the port of the fillable bladder.

2. The method of claim 1, wherein the catheter is an over-the-wire catheter.

3. The method of claim 1, wherein at least one of the fillable bladder and the filling agent is made of a bioabsorbable material.

4. The method of claim 1, wherein the filling agent is injected into the fillable bladder.

5. The method of claim 1, wherein the first side has a first side length, the second side has a second side length, the third side has a third side length, and the fourth side has a fourth side length, wherein the first side length is equal to the second side length, and wherein the third side length is equal to the fourth side length.

6. The method of claim 5, wherein the first side is symmetric with the second side with respect to a first axis of the fillable bladder and the third side is symmetric with the fourth side with respect to a second axis of the fillable bladder, wherein the first axis is perpendicular to the second axis.

7. The method of claim 1, wherein the first side is symmetric with the second side with respect to a first axis of the fillable bladder and the third side is symmetric with the fourth side with respect to a second axis of the fillable bladder, wherein the first axis is perpendicular to the second axis.

8. The method of claim 1, further comprising imaging the aneurysm space, and then sizing the filling agent according to the imaging of the aneurysm space.

9. The method of claim 1, wherein the filling agent comprises a solidifying agent.

10. A method of filling an aneurysm space within the abdominal aorta, the method comprising:

placing a prosthesis in the abdominal aorta of a subject;

delivering a fillable bladder in a deflated state into the aneurysm space using a catheter;

placing a filler tube in fluid communication with a single inflow port of the fillable bladder, wherein the filler tube provides access to an interior of the fillable bladder, and wherein the fillable bladder comprises a bladder seal surrounding the fillable bladder, wherein the bladder seal has a first side, a second side, a third side, and a fourth side, wherein at least a length of the first side is parallel to at least a length of the second side, wherein at least a length of the third side is parallel to at least a length of the fourth side, wherein at least a length of the first side is perpendicular to at least a length of the third side;

filling the fillable bladder with a filling agent through the filler tube until the fillable bladder reaches a desired size in the aneurysm space, wherein the desired size is a size which prevents dislodgment of the prosthesis and allows natural fluid flow through the prosthesis placed in the abdominal aorta and the filling agent comprises at least one of a particulate and a flowable material;

removing the filler tube from the fillable bladder; and sealing the port of the fillable bladder.

11. The method of claim 10, further comprising imaging the aneurysm space, and then sizing the filling agent according to the imaging of the aneurysm space.

12. The method of claim 10, further comprising inducing clot formation on the filling agent.

13. The method of claim 10, wherein the first side is symmetric with the second side with respect to a first axis of the fillable bladder and the third side is symmetric with the fourth side with respect to a second axis of the fillable bladder, wherein the first axis is perpendicular to the second axis.

14. The method of claim 13, wherein the first side has a first side length, the second side has a second side length, the third side has a third side length, and the fourth side has a fourth side length, wherein the first side length is equal to the second side length, and wherein the third side length is equal to the fourth side length.

15. The method of claim 10, wherein the first side has a first side length, the second side has a second side length, the third side has a third side length, and the fourth side has a fourth side length, wherein the first side length is equal to the second side length, and wherein the third side length is equal to the fourth side length.

16. The method of claim 10, wherein at least one of the fillable bladder and the filling agent is made of a bioabsorbable material.

17. The method of claim 10, wherein the filling agent comprises a solidifying agent.

* * * * *